(12) United States Patent
Meral et al.

(10) Patent No.: US 12,092,735 B2
(45) Date of Patent: Sep. 17, 2024

(54) METHOD AND APPARATUS FOR DEEP LEARNING-BASED ULTRASOUND BEAMFORMING

(71) Applicant: KONINKLIJKE PHILIPS N.V., Eindhoven (NL)

(72) Inventors: Faik Can Meral, Mansfield, MA (US); Shyam Bharat, Arlington, MA (US); Grzegorz Andrzej Toporek, Cambridge, MA (US); Carolina Amador Carrascal, Everett, MA (US); Claudia Errico, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/769,159

(22) PCT Filed: Oct. 9, 2020

(86) PCT No.: PCT/EP2020/078348
§ 371 (c)(1),
(2) Date: Apr. 14, 2022

(87) PCT Pub. No.: WO2021/074015
PCT Pub. Date: Apr. 22, 2021

(65) Prior Publication Data
US 2024/0111045 A1    Apr. 4, 2024

Related U.S. Application Data

(60) Provisional application No. 62/915,672, filed on Oct. 16, 2019.

(51) Int. Cl.
*G01S 15/89* (2006.01)
*G01S 7/52* (2006.01)

(52) U.S. Cl.
CPC ...... *G01S 15/8968* (2013.01); *G01S 7/52028* (2013.01)

(58) Field of Classification Search
CPC ............. G01S 15/8968; G01S 7/52028; G01S 7/52047; G01S 15/8915; G01S 7/52087;
(Continued)

(56) References Cited

U.S. PATENT DOCUMENTS 11,829,872 B2 * 11/2023 Zheng ...................... G06N 3/08
11,950,960 B2 * 4/2024 Vignon ................ A61B 8/5207
(Continued)

FOREIGN PATENT DOCUMENTS

CN    113454484 A  *  9/2021  .......... A61B 8/5207
CN    114554969 A  *  5/2022  .......... A61B 8/0883
(Continued)

OTHER PUBLICATIONS

International Search Report and Written Opinion for PCT/EP2020/078348; Mailing date: Jan. 22, 2021, 13 pages.
(Continued)

*Primary Examiner* — Daniel Pihulic

(57) ABSTRACT

Ultrasound image devices, systems, and methods are provided. An ultrasound imaging system, comprising an array of acoustic elements configured to transmit ultrasound energy into an anatomy in accordance with a first preset acquisition setting, and to receive ultrasound echoes associated with the anatomy; and a processor circuit in communication with the array of acoustic elements and configured to receive, from the array, ultrasound channel data corresponding to the received ultrasound echoes; generate a first set of beamformed data by applying a predictive network to the ultrasound channel data, wherein the first set of beamformed data is associated with a second preset acquisition setting different than the first preset acquisition setting;
(Continued)

generate an image of the anatomy from the first set of beamformed data; and output, to a display in communication with the processor circuit, the image of the anatomy.

20 Claims, 12 Drawing Sheets

(58) Field of Classification Search
CPC ..... A61B 8/4483; A61B 8/488; A61B 8/0883; A61B 8/5207
See application file for complete search history.

(56) References Cited

U.S. PATENT DOCUMENTS

| | | | |
|---|---|---|---|
| 2013/0237272 A1* | 9/2013 | Prasad | H01Q 1/245 342/372 |
| 2014/0128032 A1* | 5/2014 | Muthukumar | H04W 52/0254 455/412.2 |
| 2017/0262598 A1 | 9/2017 | Petkov et al. | |
| 2017/0347993 A1 | 12/2017 | Anand | |
| 2018/0177461 A1 | 6/2018 | Bell et al. | |
| 2021/0064993 A1* | 3/2021 | Zheng | G01S 7/52079 |
| 2021/0265042 A1* | 8/2021 | Kim | A61B 8/5246 |
| 2022/0096054 A1* | 3/2022 | Vignon | A61B 8/5207 |
| 2022/0401062 A1* | 12/2022 | Naidu | A61B 8/085 |
| 2023/0148996 A1* | 5/2023 | Arntfield | A61B 8/4427 600/437 |
| 2023/0414111 A1* | 12/2023 | Sun | G06T 7/0012 |
| 2024/0111045 A1* | 4/2024 | Meral | G01S 15/8968 |

FOREIGN PATENT DOCUMENTS

| | | | | |
|---|---|---|---|---|
| CN | 115330681 A | * | 11/2022 | |
| CN | 115761452 A | * | 3/2023 | |
| EP | 3928121 A1 | * | 12/2021 | ........... A61B 8/5207 |
| EP | 4045940 A1 | * | 8/2022 | ........... A61B 8/0883 |
| WO | 2013082426 A1 | | 6/2013 | |
| WO | WO-2020016449 A1 | * | 1/2020 | ............ A61B 8/145 |
| WO | WO-2020169384 A1 | * | 8/2020 | ........... A61B 8/5207 |
| WO | WO-2021074015 A1 | * | 4/2021 | ........... A61B 8/0883 |
| WO | WO-2021099278 A1 | * | 5/2021 | ........... A61B 8/0833 |

OTHER PUBLICATIONS

Luijten, B. et al., "Adaptive Ultrasound Beamforming using Deep Learning", arXiv:1909.10342, 2019, 10 pages.
Vedula, S. et al., "High quality ultrasonic multi-line transmission through deep learning", arXiv:1808.07819, 2018, 11 pages.
Creswell, A. et al., "Generative Adversarial Networks: An Overview," EEE Signal Processing Magazine, 2018, vol. 35, No. 1, pp. 53-65.
Johnson, J. et al., "Perceptual Losses for Real-Time Style Transfer and Super-Resolution", arXiv:1603.08155, 2016, 18 pages.
Luchies A. C. et al., "Deep Neural Networks for Ultrasound Beamforming," IEEE Transactions on Medical Imaging, 2018, vol. 37, No. 9, pp. 2010-2021.
Lucas, A. et al., "Using Deep Neural Networks for Inverse Problems in Imaging: Beyond Analytical Methods," IEEE Signal Processing Magazine, 2018, vol. 35, No. 1, pp. 20-36.
Girshick, R.; "Fast R-CNN", arXiv:1504.08083, 2015, 9 pages.
He, K. et al., "Mask R-CNN", arXiv:1703.06870, 2018, 12 pages.
Isola, P. et al., "Image-to-Image Translation with Conditional Adversarial Networks," IEEE Conference on Computer Vision and Pattern Recognition (CVPR), 2017, pp. 5967-5976.
Redmon, J. et al., "You Only Look Once: Unified, Real-Time Object Detection", arXiv:1506.02640, 2016, 10 pages.
Goodfellow, I. et al., "Generative Adversarial Nets", arXiv:1406.2661, 2014, 9 pages.

* cited by examiner

METHOD AND APPARATUS FOR DEEP LEARNING-BASED ULTRASOUND BEAMFORMING

CROSS-REFERENCE TO PRIOR APPLICATIONS

This application is the U.S. National Phase application under 35 U.S.C. § 371 of International Application No. PCT/EP2020/078348, filed on Oct. 9, 2020, which claims the benefit of U.S. Provisional Patent Application No. 62/915,672 filed on Oct. 16, 2019. These applications are hereby incorporated by reference herein.

TECHNICAL FIELD

The present disclosure relates generally to ultrasound imaging and, in particular, to reconstructing ultrasound images from ultrasound echo channel responses using predictive models for beamforming.

BACKGROUND

Ultrasound imaging systems are widely used for medical imaging. A conventional medical ultrasound system may include an ultrasound transducer probe coupled to a processing system and one or more display devices. The ultrasound transducer probe may include an array of acoustic elements that transmit acoustic waves into an object (e.g., a patient's body) and record acoustic waves reflected from the object. The transmission of the acoustic waves and/or the reception of reflected acoustic waves or echo responses may be performed by the same set of ultrasound transducer elements or different sets of acoustic elements. The processing system reconstructs or creates an image of the object from the echo responses received by the acoustic elements. For conventional ultrasound imaging, the processing system may perform beamforming by delaying and summing the received echo response signals to achieve receive focusing along imaging depths. The processing system may reconstruct the image from the beamformed signals by applying signal processing and/or image processing techniques.

Ultrasound imaging of dynamic anatomical features, such as the heart, is challenging due to the difficulties of finding a sufficient acoustic window and maintaining acoustic coupling, which requires pinpointing optimal acoustic and acquisition settings for imaging the feature(s). Existing ultrasound software often includes tissue-specific presets (TSPs) designed to facilitate the image acquisition process by providing selectable sets of default acoustic and acquisition parameters and/or signal processing pathways. However, a predefined TSP often fails to produce quality images, especially for gated sequences, e.g., over the full cardiac cycle, thus forcing the user to make additional imaging adjustments or toggle between multiple TSPs in search of the TSP capable of producing the best images. Even then, synchronous comparison of the images obtained using different TSPs is often impossible and time-consuming, making it difficult for the user to choose the optimal TSP for a given anatomical feature. Thus, the ultrasound image quality in conventional ultrasound imaging systems may be limited by the capability of the acquisition process.

SUMMARY

While existing ultrasound imaging has proved useful for clinical guidance and diagnosis, there remains a need for improved systems and techniques for providing high-quality ultrasound images. For example, the long list of acoustic and acquisition parameters that may be selected and adjusted by a user may be difficult to fully consider and choose during an ultrasound exam, even if such parameters are organized into predefined TSPs, a complication exacerbated by the lack of synchronous side-by-side comparisons of images obtained using previous and current parameters. Embodiments of the present disclosure provide systems arranged to assist the user in choosing optimal acoustic and/or acquisition settings on an ultrasound apparatus for imaging a targeted anatomical feature by simultaneously acquiring and reconstructing images using a predefined set of different TSPs or acoustic/acquisition setting configurations. While specific examples are discussed herein with respect to cardiac ultrasound imaging, embodiments are not limited to echocardiography, and may also apply to imaging any other anatomical feature, including but not limited to organs such as the lungs, kidney or liver. Embodiments may be particularly advantageous for imaging dynamic features, such as the heart and lungs.

Examples provide a deep learning framework to map ultrasound echo channel signals to beamformed signals corresponding to different TSPs in addition to or instead of performing conventional delay-and-sum (DAS)-based beamforming. Deep learning-based beamforming may produce beamformed data characteristic of multiple TSPs without reducing the frame rate during data acquisition and without disrupting user workflow. Cine-loops of the targeted feature(s) imaged with different settings may then be compared to find the optimal image setting for each patient or diagnostic purpose. A user may select the optimal TSP and continue an exam without manually performing iterative imaging adjustments. In various examples, an imaging probe including a transducer array may be used for ultrasound imaging. The transducer array may include an array of acoustic elements that emit ultrasound pulses into an object (e.g., a patient's anatomy) and receive ultrasound channel signals corresponding to ultrasonic waves reflected from the object. A predictive network (e.g., a convolutional neural network (CNN)) may be trained to map the per-channel ultrasound echo channel signals to beamformed signals on a pixel-by-pixel or line-by-line basis. The predictive network may include multiple neural networks, each neural network arranged to generate beamformed data corresponding to a specific TSP, which may be different than the TSP used to acquire the original echo signal input. In some embodiments, the predictive network may be trained to provide beamformed signals corresponding to multiple TSPs at multiple timepoints. The resulting beamformed signals corresponding to different TSPs may be displayed simultaneously for viewing, comparison and/or selection by a user. The predictive network may be trained using a combination of simulation data, data acquired from phantoms in experimental test setups, and/or data acquired from patients in clinical settings. The disclosed embodiments are suitable for use in two-dimensional (2D) imaging, three-dimensional (3D) volumetric imaging, focused imaging, and/or unfocused imaging.

In accordance with embodiments of the present disclosure, an ultrasound imaging system may include an array of acoustic elements arranged to transmit ultrasound energy into an anatomy in accordance with a first preset acquisition setting and to receive ultrasound echoes associated with the anatomy. The system may also include a processor circuit in communication with the array of acoustic elements. The processor circuit may be arranged to receive, from the array, ultrasound channel data corresponding to the received ultrasound echoes; generate a first set of beamformed data by applying a predictive network to the ultrasound channel data, wherein the first set of beamformed data is associated with a second preset acquisition setting different than the first preset acquisition setting; generate an image of the anatomy from the first set of beamformed data; and output, to a display in communication with the processor circuit, the image of the anatomy.

In some examples, the processor circuit may be further arranged to generate a second set of beamformed data by applying the predictive network to the ultrasound channel data, wherein the second set of beamformed data is associated with a third preset acquisition setting different than the first preset acquisition setting and the second acquisition setting. In some embodiments, the processor circuit may be further arranged to process the channel data for generating the second set of beamformed data in parallel with the first set of beamformed data. In some examples, the predictive network comprises first and second neural networks, arranged in parallel to receive the channel data and output a respective one of the first and second sets of beamformed data. In some embodiments, the first and second preset acquisition settings are each applied for a single acquisition frame.

In some examples, the processor circuit may be further arranged to generate an image of the anatomy from the second set of beamformed data; and output, to a display in communication with the processor circuit, the image of the anatomy from the second set of beamformed data simultaneously with the image of the anatomy from the first set of beamformed data. In some embodiments, the predictive network may be trained by providing test ultrasound channel data generated based on the first preset acquisition setting and first target beamformed data generated based on the second preset acquisition setting; and training the predictive network to produce the first target beamformed data from the test ultrasound channel data. In some examples, the predictive network may be trained by providing second target beamformed data generated based on the first preset acquisition setting; and training the predictive network to produce the second target beamformed data from the test ultrasound channel data before training the predictive network to produce the first target beamformed data. In some examples, the array of acoustic elements includes a one-dimensional array of acoustic elements or a two-dimensional array of acoustic elements.

In accordance with embodiments of the present disclosure, a method of ultrasound imaging may involve transmitting ultrasound energy into an anatomy in accordance with a first preset acquisition setting receiving ultrasound echoes associated with the anatomy; receiving ultrasound channel data corresponding to the received ultrasound echoes; generating a first set of beamformed data by applying a predictive network to the ultrasound channel data, wherein the first set of beamformed data is associated with a second preset acquisition setting different than the first preset acquisition setting; generating an image of the anatomy from the first set of beamformed data; and outputting the image of the anatomy.

In some examples, the method may further involve generating a second set of beamformed data by applying the predictive network to the ultrasound channel data, wherein the second set of beamformed data is associated with a third preset acquisition setting different than the first preset acquisition setting and the second acquisition setting. In some embodiments, the method may further involve processing the channel data for generating the second set of beamformed data in parallel with the first set of beamformed data. In some examples, the predictive network includes first and second neural networks, arranged in parallel to receive the channel data and output a respective one of the first and second sets of beamformed data. In some embodiments, the first and second preset acquisition settings are each applied for a single acquisition frame. In some examples, the method further involves generating an image of the anatomy from the second set of beamformed data; and outputting the image of the anatomy from the second set of beamformed data simultaneously with the image of the anatomy from the first set of beamformed data. In some embodiments, the method further involves training the predictive network by providing test ultrasound channel data generated based on the first preset acquisition setting and first target beamformed data generated based on the second preset acquisition setting; and training the predictive network to produce the first target beamformed data from the test ultrasound channel data. In some examples, training the predictive network further involves providing second target beamformed data generated based on the first preset acquisition setting; and training the predictive network to produce the second target beamformed data from the test ultrasound channel data before training the predictive network to produce the first target beamformed data. In some examples, the array of acoustic elements includes a one-dimensional array of acoustic elements or a two-dimensional array of acoustic elements.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
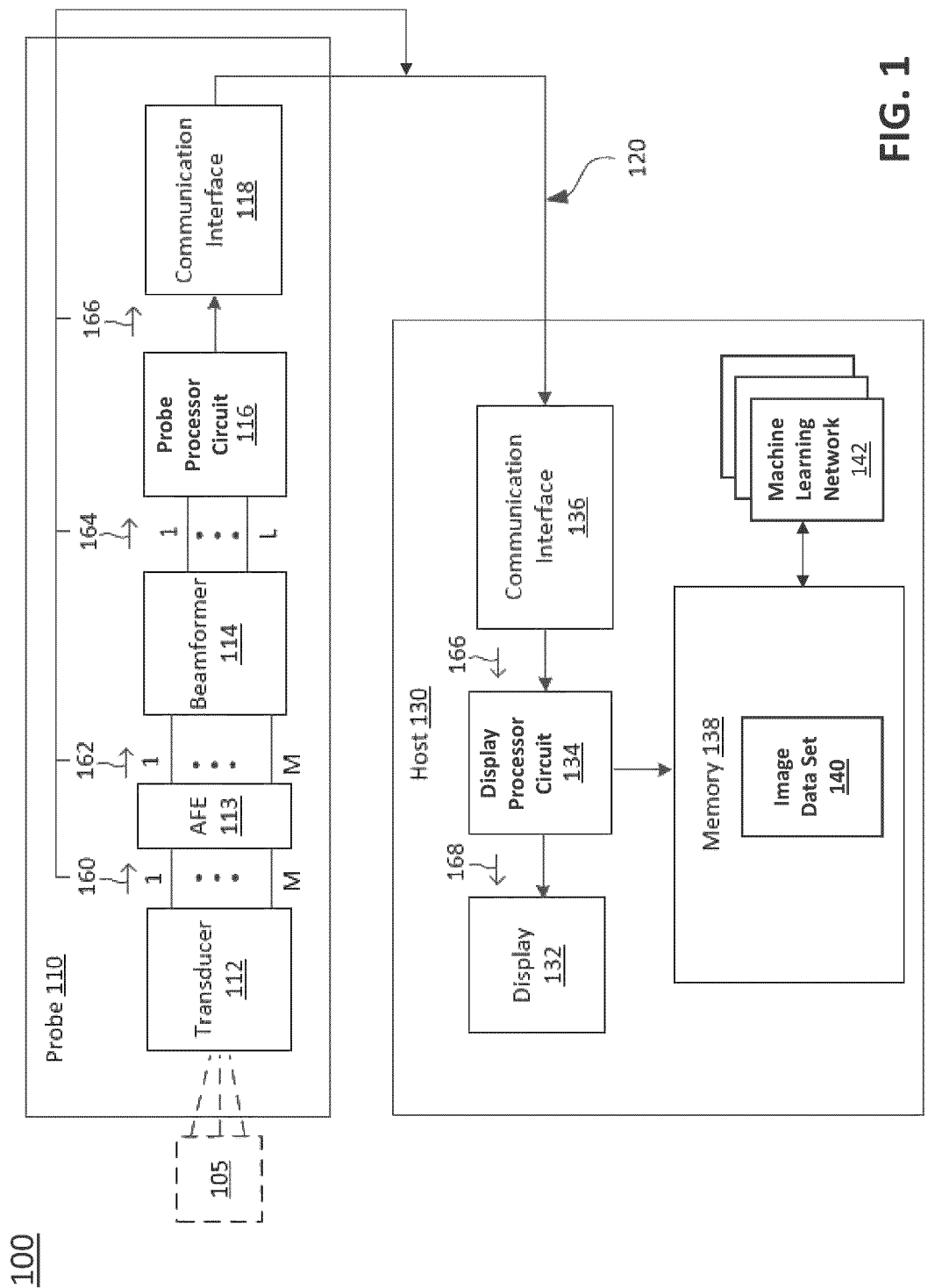
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations and variations of these combinations will not be described separately.

FIG. 1 is a schematic diagram of a system 100 arranged to perform ultrasound imaging, according to aspects of the present disclosure. The system 100 is used for scanning an area or volume of a patient's body. The system 100 includes a probe 110 in communication with a host 130 over a communication interface or link 120. The probe 110 includes a transducer 112, an analog front end (AFE) 113, a beamformer 114, a processor component, i.e., a processor circuit 116, and a communication interface 118. The host 130 includes a display 132, a display processor circuit 134, a communication interface 136, and a memory 138. Memory 138 may comprise any suitable storage device, such as cache memory (e.g., a cache memory of the processor circuit 134), random access memory (RAM), magnetoresistive RAM (MRAM), read-only memory (ROM), programmable read-only memory (PROM), erasable programmable read-only memory (EPROM), electrically erasable programmable read-only memory (EEPROM), flash memory, solid state memory device, hard disk drives, solid state drives, other forms of volatile and non-volatile memory, or a combination of different types of memory.

The probe 110 may be in any suitable form for imaging various body parts of a patient, e.g., the heart or kidneys, while positioned inside or outside of the patient's body. In an embodiment, the probe 110 is an external ultrasound imaging device including a housing arranged for handheld operation by a user. The transducer 112 may be arranged to obtain ultrasound data while the user grasps the housing of the probe 110 such that the transducer 112 is positioned adjacent to and/or in contact with a patient's skin. The probe 110 is arranged to obtain ultrasound data of anatomy within the patient's body while the probe 110 is positioned outside of the patient's body. In some other embodiments, the probe 110 may be in the form of a catheter, an intravascular ultrasound (IVUS) catheter, an intracardiac echocardiography (ICE) catheter, a transesophageal echocardiography (TEE) probe, a transthoracic echocardiography (TTE) probe, an endo-cavity probe, a handheld ultrasound scanner, or a patch-based ultrasound device.

Typically transducer 112 emits ultrasound signals towards an anatomical object 105 and receives echo signals reflected from the object 105 back to the transducer 112. In some embodiments (not shown) transducer 112 may emit ultrasound signals and a second receiver transducer may receive the echo signals. The object 105 may include any anatomy (e.g., heart, lung, blood vessel, tissues, kidney, and/or liver) of a patient that is suitable for ultrasound imaging examination.

The ultrasound transducer 112 may include any suitable number of acoustic elements, including one or more acoustic elements and/or plurality of acoustic elements. In some instances, the transducer 112 includes a single acoustic element. In some instances, the transducer 112 may include an array of acoustic elements with any number of acoustic elements in any suitable configuration. For example, the transducer 112 may include between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. In some instances, the transducer 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) may be uniformly or independently controlled and activated. The transducer 112 may be arranged to obtain 1D, 2D, and/or three-dimensional (3D) images of patient anatomy. The acoustic elements may also be referred to as transducer elements or imaging elements. In some embodiments, the transducer 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The AFE 113 is coupled to the transducer 112. The AFE 113 may include components that control the transmissions of ultrasound waves at the transducer 112 and/or the receptions of echo responses at the transducer 112. For example, in a transmit path, the AFE 113 may include a digital-to-analog converter (DAC), filters, gain controls, and/or a high-voltage (HV) transmitter that drives or triggers ultrasound pulse emissions at the acoustic elements or transducer elements of the transducer 112. In a receive path, the AFE 113 may include gain controls, filters, amplifiers, and/or analog-to-digital converts (ADCs) that receive echo responses from the transducer elements of the transducer 112. The AFE 113 may further include a plurality of transmit/receive (T/R) switches that control the switching between transmit and receive at the transducer elements and prevent the high-voltage pulses from damaging the transducer elements for the transducer 112.

Figure 2:
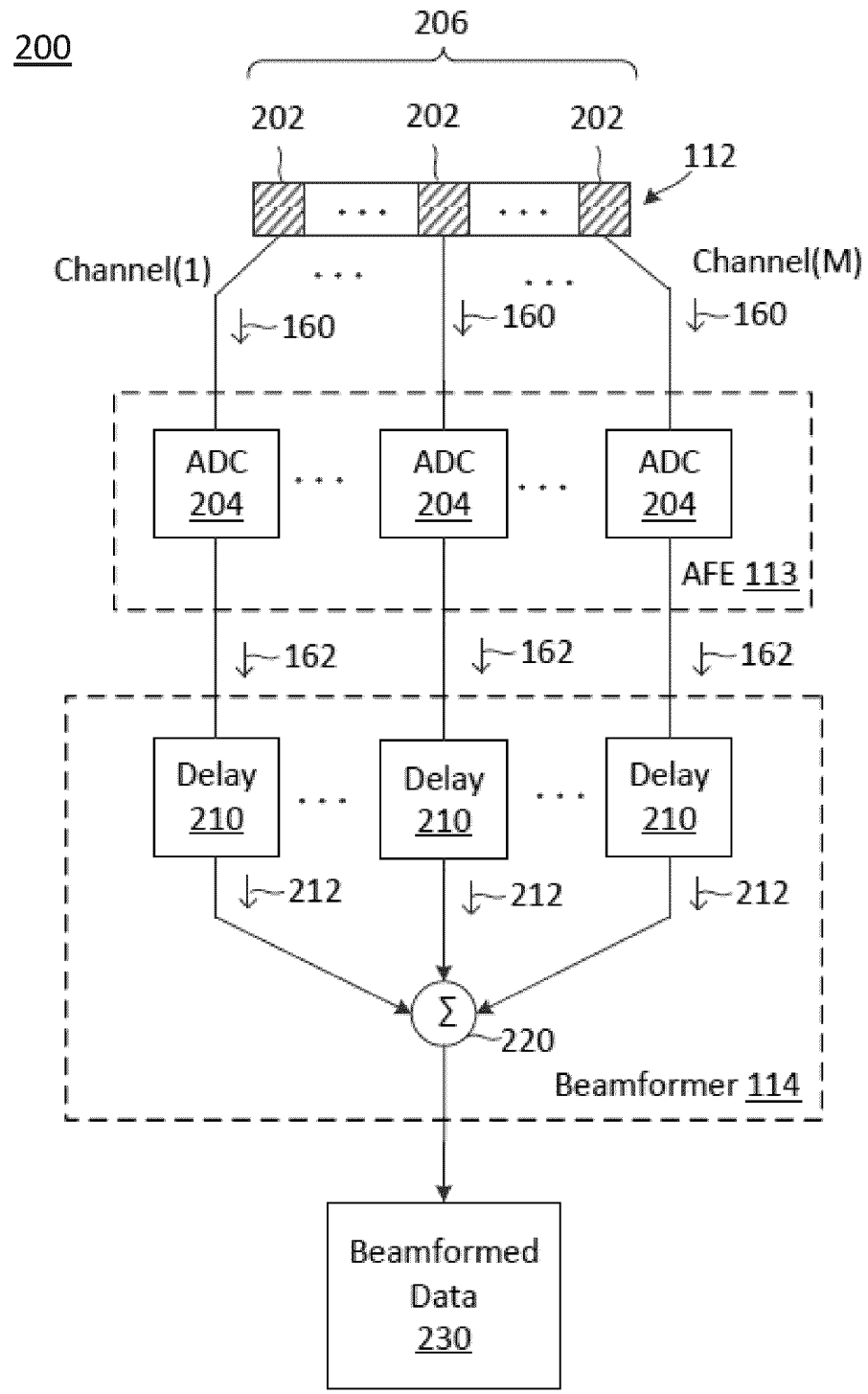
FIG. 2 is a schematic diagram of an ultrasound imaging system implementing delay-and-sum (DAS)-based beamforming, according to embodiments of the present disclosure.

In an embodiment, the transducer 112 includes M plurality of transducer elements (e.g., acoustic elements 202 of FIG. 2). In some embodiments, M may be about 2, 16, 64, 128, 192, or greater than 192. In the receive path, each transducer element may convert ultrasound energy received from a reflected ultrasound pulse to an electrical signal, forming a single receive channel. In other words, the transducer 112 may generate M analog ultrasound echo channel signals 160. The AFE 113 may be coupled to the transducer 112 via M signal lines. The ADCs (e.g., ADCs 204 of FIG. 2) in the AFE 113 may produce M digital ultrasound echo channel signals 162, each corresponding to an analog ultrasound echo channel signal 160 received at one of the transducer element in the transducer 112. The digital ultrasound echo channel signals 162 may also be referred to as ultrasound echo data streams or ultrasound echo channel data.

The beamformer 114 is coupled to the AFE 113. The beamformer 114 may include delay elements and summing elements arranged to control transmit and/or receive beamforming at the transducer 112. The beamformer 114 may apply appropriate time-delays to at least a subset of the digital ultrasound echo channel signals 162 and combine the time-delayed digital ultrasound echo channel signals to form a beamformed signal 164 (e.g., a focused beam). For example, the beamformer 114 may produce L plurality of beamformed signals 164, where L is a positive integer smaller than M.

In some embodiments, the beamformer 114 may include multiple stages of beamforming. For example, the beamformer 114 may perform partial beamforming to combine a subset of the digital ultrasound echo channel signals 162 to form partially beamformed signals and subsequently beamform the partial beamformed signals to produce fully beamformed signals. While the beamformer 114 is described in the context of digital beamforming, in some embodiments, the AFE 113 may include electronics and/or dedicated hardware for analog partial beamforming. In some examples, multiple hardware beamformers 114 may be included, each beamformer arranged to operate in accordance with a specific TSP.

The communication interface 118 is coupled to the probe processor circuit 116, which can be configured to generate image signals 166 from the beamformed signals 164 generated by the beamformer 114. The communication interface 118 may include one or more transmitters, one or more receivers, one or more transceivers, and/or circuitry for transmitting and/or receiving communication signals. The communication interface 118 may include hardware components and/or software components implementing a particular communication protocol suitable for transporting signals over the communication link 120 to the host 130. The communication interface 118 may be referred to as a communication device or a communication interface module. The communication interface 118 may be implemented by a processor, such as the processor 1100 shown in FIG. 11.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the transducer element signals (e.g., the analog ultrasound echo channel signals 160), the image signals 166, or partially beamformed signals. Appropriate connections are now shown. The communication interface 136 may be substantially similar or identical to the communication interface 118. The host 130 may be any suitable computing and display device, such as a workstation, a personal computer (PC), a laptop, a tablet, or a mobile phone.

The display processor circuit 134 is coupled to the communication interface 136. The display processor circuit 134 may be implemented as a combination of software components and hardware components, for example as described in FIG. 11. The display processor circuit 134 may include a central processing unit (CPU), a graphics processing unit (GPU), a digital signal processor (DSP), an application-specific integrated circuit (ASIC), a controller, a FPGA device, another hardware device, a firmware device, or any combination thereof arranged to perform the operations described herein. The display processor circuit 134 may also be implemented as a combination of computing devices, e.g., a combination of a DSP and a microprocessor, a plurality of microprocessors, one or more microprocessors in conjunction with a DSP core, or any other such configuration.

The display processor circuit 134 may be arranged to generate or reconstruct images 168 of the object 105 from the image signals 166 received from the probe 110, beamformed images 168 from transducer signals (e.g., the analog ultrasound echo channel signals 160), or partially beamformed signals 164. The processor circuit 134 may further apply image processing techniques to the image signals 166. In some embodiments, the display processor circuit 134 may perform scan conversions to form 2D or 3D volume images from the image signals 166. In some embodiments, the processor circuit 134 may perform real-time processing on the image signals 166 to provide a streaming video of ultrasound images 168 of the object 105. In some examples, the display processor circuit 134 may generate one or more cine-loops, each cine-loop comprised of a certain number of image frames. According to such examples, each cine-loop may correspond to one gated sequence, e.g., one cardiac cycle or one respiratory cycle. The display processor circuit 134 may be arranged to generate multiple cine-loops, each cine-loop generated according to a specific TSP. The display processor circuit 134 may also be arranged to generate multiple images, videos and/or cine-loops for simultaneous display on the display 132, each image corresponding to a specific timepoint and/or TSP.

As further described in connection with FIG. 10, the display processor circuit 134 may also be arranged to generate composite ultrasound images of the object 105 by blending image data acquired using multiple TSPs. The images 168 may include morphological information, functional information, and/or quantitative measurement of the object 105 depending on the acquisition modalities used at the probe 110. The morphological information may include anatomical structural information (e.g., B-mode information) of the object 105. Examples of functional information may include tissue strain, elasticity, Doppler flow, tissue Doppler flow, and/or blood flow information associated with the object 105. Examples of quantitative measurements may include a blood flow velocity, blood flow volume, lumen diameter, lumen area, stenosis length, plaque burden, and/or tissue elasticity. In some embodiments, the display processor circuit 134 may perform image analysis on the image signals 166 to determine clinical conditions associated with the object 105. The display processor circuit 134 may also be arranged to overlay various indicators, e.g., bounded boxes, identifying one or more features of interest, e.g., a feature captured with optimal quality using a particular TSP.

The display 132 is coupled to the display processor circuit 134. The display 132 may be a user interface, monitor or any suitable display. In some examples, the display 132 may be a touch screen arranged to display various images and receive one or more user inputs. The display 132 may be arranged to display ultrasound images, image videos, cine-loops, and/or information associated with the object 105 under examination.

While the system 100 is illustrated with beamforming and signal processing functions performed by the beamformer 114 and the probe processor circuit 116, respectively, at the probe 110, in some embodiments, at least some of the beamforming and/or signal processing functions may be performed at the host 130. In other words, the probe 110 may transfer digital ultrasound echo channel signals 162 or beamformed signals 164 to the host 130 for processing. In some other embodiments, the probe 110 may transfer the analog ultrasound echo channel signals 160, for example, with some gain controls, filtering, and/or partial analog beamforming to the host 130 for processing. In such embodiments, the host 130 may further include ADCs and a beamformer. In addition, the communication interface 118 at the probe 110 may be an industry standard physical connector and/or a proprietary physical connector and the communication link 120 may include any industry standard cables, coaxial cables, and/or proprietary cables. The system 100 may represent any type of ultrasound imaging system, where ultrasound imaging functionalities may be partitioned in any suitable manner across a probe (e.g., including a transducer 112), a host, and/or any intermediate processing subsystem between the probe and the host.

According to embodiments of the present disclosure, the system 100 may use one or more predictive models (e.g., a deep learning model) for beamforming in addition to or instead of the delay-and-sum (DAS)-based beamforming described above. The system 100 may be used in various stages of ultrasound imaging. In an embodiment, the system 100 may be used for collecting ultrasound images to form a training dataset 140 for training a machine learning network 142 for ultrasound beamforming. For example, the host 130 may include a memory 138, which may be any of the forms of memory disclosed above. The memory 138 may be arranged to store the training image dataset. For example, the training image dataset 140 may store the digital ultrasound echo channel signals 162 in association with beamformed signals generated using the system 100 or simulated beamformed signals.

In an embodiment, the system 100 may utilize the trained machine learning network 142 for beamforming instead of or in addition to the DAS beamformer 114 in a clinical setting (e.g., during an ultrasound examination). In some embodiments, the machine learning network 142 may comprise a multilayered network, each layer trained to map input channel data to beamformed signals having characteristics corresponding to a specific TSP, which may be different than the TSP used to acquire the input channel data. Examples may also include multiple neural networks, e.g., CNNs, arranged within the machine learning network 142, each individual neural network trained to map input channel data to beamformed signals having characteristics corresponding to a specific TSP.

In some examples, the machine learning network 142 may comprise a generative network. Such a network may include a generative model trained to capture input channel data distribution, and a discriminative model trained to estimate the probability that a given data set is derived from training data versus the generative model. For example, the generative model may process a beamformed image reconstructed with a specific TSP and synthesize an output image corresponding to a different TSP. Mechanisms for training a deep learning model for ultrasound beamforming and applying the trained deep learning model for ultrasound beamforming are described in greater detail herein.

FIG. 2 is a schematic diagram illustrating an ultrasound imaging system 200 implementing DAS-based beamforming, according to embodiments of the present disclosure. The system 200 corresponds to a portion of the system 100 and provides a more detailed view of components along the receive signal path of the system 100 (e.g., within the probe 110 and/or the host 130). As shown in FIG. 2, the transducer 112 may include a plurality of acoustic elements 202. Typically transducer 112 would transmit one or more acoustic waves into an object. The reflection of the acoustic wave from the object are the receive echoes. Each acoustic element 202 forms a receive channel, where an analog ultrasound echo channel signal 160 may be received when the acoustic element 202 is activated for receiving after a transmit trigger, i.e., after transmission of one or more ultrasonic pulses. For example, the transducer 112 may include M quantity of acoustic elements 202. Thus, the receive channels may be referred to as Channel(1) to Channel(M). In an embodiment, the AFE 113 may include a plurality of ADCs 204. Each ADC 204 may be coupled to an acoustic element 202. The AFE 113 may additionally include other components, such as filters and amplifiers, coupled to each acoustic element 202. Each ADC 204 may sample a corresponding analog ultrasound echo channel signal 160 to form a digital ultrasound echo channel signal 162. Each digital ultrasound echo channel signal 162 includes a series of samples along an imaging depth of field. In some embodiments, the AFE 113 may include less ADCs 204 than the number of receive channels. In such embodiments, each ADC 204 may be coupled to a subset of the receive channels and arranged to sample analog ultrasound echo channel signals 160 from the subset of receive channels, for example, in a multiplexed manner.

The beamformer 114 is coupled to the AFE 113. The beamformer 114 includes a plurality of delay elements 210 each coupled to an ADC 204. All of delay elements 210 are coupled to a summing element 220. Each delay element 210 is arranged to apply a time-delay to a corresponding digital ultrasound echo channel signal 162 to produce a delayed ultrasound echo channel signal 212. The delay elements 210 may be dynamically arranged to apply appropriate time-delays to the digital ultrasound echo channel signal 162. For example, one or more of the acoustic elements 202 may be triggered to transmit ultrasonic energy into an anatomy (e.g., the anatomy object 105) and a group of acoustic elements 202 may be activated to receive ultrasound echoes reflected from the anatomy due to the ultrasound signal transmission. Due to the different propagation paths, receive echoes may arrive at the acoustic elements 202 at different times. Thus, the delay elements 210 delay the ultrasound echo channel signals 162 such that the ultrasound echo channel signals 162 are all aligned in time. The summing element 220 is arranged to combine the delayed ultrasound echo channel signals 212 to produce beamformed data 230. The beamformed data 230 corresponds to the beamformed signals 164.

The delay elements 210 may be paired with a single ADC 204 or with multiple ADCs 204. Likewise, a single ADC 204 may be connected with multiple delay elements 210. In some embodiments, multiple arrangements of ADC 204 and delay elements 210 may be configured to permit different utilization of the equipment depending on, for example, desired frame rates or ultrasound study being imaged.

In general, the goal of beamforming is to reverse the acoustic wave propagation effect so that ultrasound or acoustic energy may be focused at various locations along a main axis of the ultrasound echo signal path. For example, the delay elements 210 may be dynamically arranged to provide receive focusing at each echo location along the main axis of the ultrasound echo signal path. In other words, the delay elements 210 may be arranged with different delays to provide focusing at different echo locations.

The beamformed data 230 may be further processed by the probe processor circuit 116 and/or the display processor circuit 134, for example, including frequency compounding, envelope detection, logarithmic compression, and/or non-linear image filtering as described above with respect to FIG. 1, to produce an image 168.

Some performance measures, such as image quality or resolution and/or data acquisition rate or frame rates, may be important for ultrasound imaging. For example, the image quality, resolution, or contrast may impact a clinician's ability to differentiate anatomical details within an acquired ultrasound image. The data acquisition rate or frame rates may impact the amount of time required for acquiring an ultrasound image or video, and thus the real-time imaging capability and ultrasound examination time.

The present disclosure may use deep learning techniques for beamforming in conjunction with conventional DAS-based beamforming. In some embodiments, a machine learning network is trained to map per-channel ultrasound echo data (e.g., the ultrasound echo channel signals 162) generated using a certain TSP to beamformed data corresponding to a different TSP. As a result, the deep learning-based beamformed data may include image properties corresponding to images generated using acoustic and/or acquisition parameters that are different than the parameters actually used to obtain the original channel data. Acoustic parameters may include ultrasound pulse shape, sequence or frequency, and acquisition parameters may include line density, resolution, contrast, and/or speckle, for example.

Figure 3:
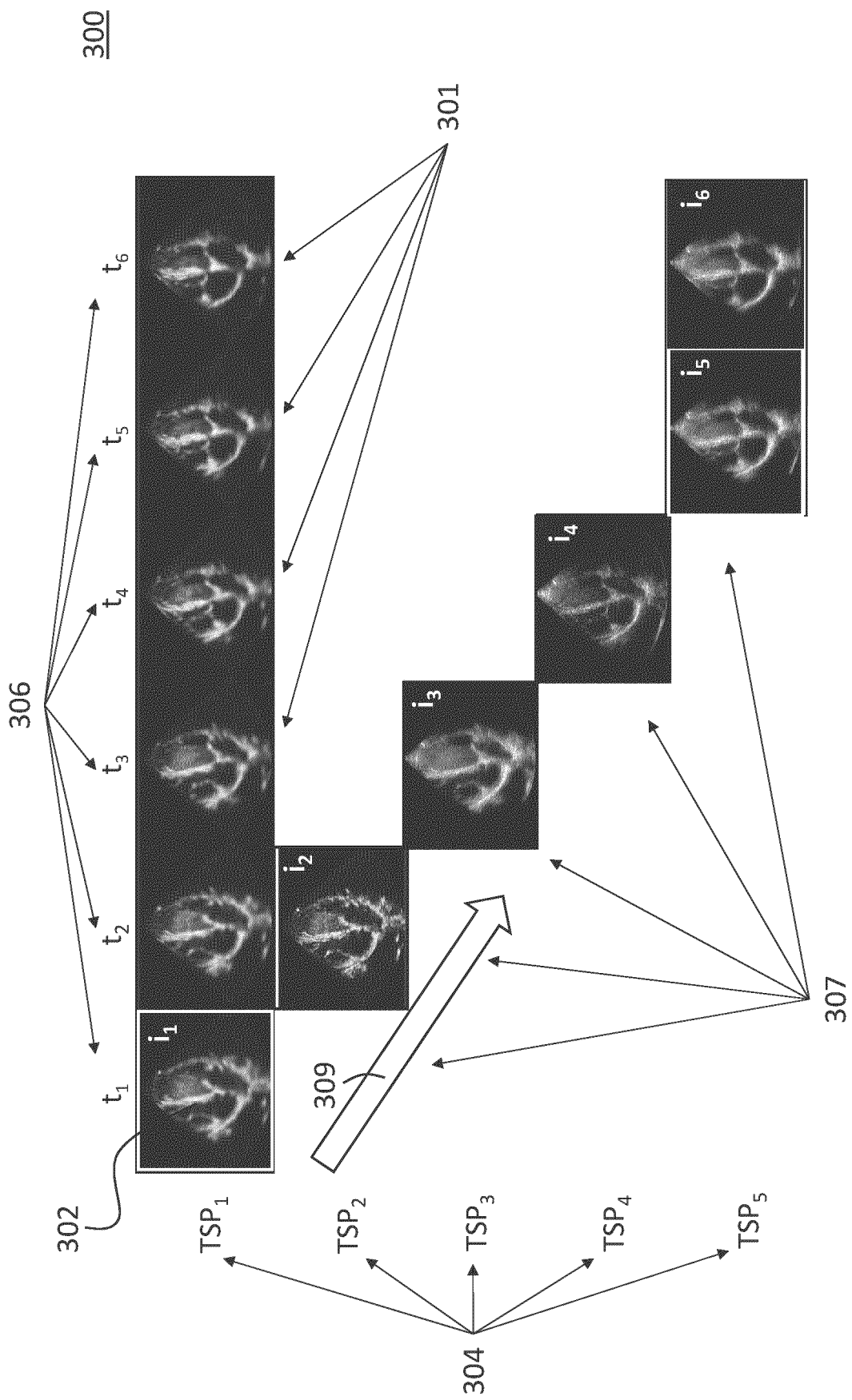
FIG. 3 is a schematic diagram of an image acquisition scheme, according to embodiments of the present disclosure.

FIG. 3 is a schematic diagram of an image acquisition scheme 300 implemented in accordance with embodiments of the present disclosure. The image acquisition scheme 300, which is portrayed as a matrix for illustration purposes only, includes horizontally arranged images 301 of a heart 302 acquired over multiple timepoints 306 ($t_1$-$t_6$) using one of multiple different TSPs 304, and diagonally arranged images 307 ($i_1$-$i_6$) acquired sequentially in the direction of arrow 309 over multiple timepoints 306 ($t_1$-$t_6$) using each of the different TSPs 304 ($TSP_{1-5}$), each TSP defined by a unique set of acoustic and acquisition parameters.

The horizontally arranged images 301 and diagonally arranged images 307 ($i_1$-$i_6$) may be acquired during different iterations of the same gated sequence, e.g., a cardiac cycle, such that two images are not acquired simultaneously at each of timepoints $t_2$-$t_6$, but rather at the same timepoint of separate iterations of the same sequence. The image acquisition scheme 300 may be implemented to acquire the initial data utilized by one or more predictive networks to perform deep learning-based beamforming, thereby generating additional images (shown in FIG. 4) without additional image acquisition.

The image acquisition scheme 300 initially involves acquiring a plurality of images 301 over time using a single fixed or default TSP, here $TSP_1$, and performing DAS-based beamforming using the acquired image data. The fixed TSP may be applied for a single gated sequence, e.g., one cardiac cycle, less than a gated sequence, more than a gated sequence, or any period therebetween. The ultrasound system used to acquire the images (e.g., system 100 or 200) may also be arranged to rapidly switch TSPs 304 from one image frame to the next. In some embodiments, each of the different TSPs 304 may be utilized for only one frame. The transition between frame-by-frame TSP switching and imaging at a single, fixed TSP may be initiated by a user or automatically according to a stored setting. For example, the ultrasound system may be arranged to restore a constant, fixed TSP after utilizing TSP switching for one, two, three or more gated sequences. The acquisition period may continue for one or more gated sequences (e.g., one or more cardiac cycles, such as 2, 3, or 4 cycles, or more), which may be specified or controlled by the user. Alternatively, the acquisition period may continue indefinitely for real-time visualization of multiple images at the same time.

In the example shown, the images 307 acquired using $TSP_{S1-5}$ are obtained at six discrete timepoints 306 ($t_{1-6}$), each timepoint corresponding to a phase of the cardiac cycle. An ultrasound transducer (e.g., ultrasound transducer 112) may acquire the data used to generate the diagonally arranged images 307 by transmitting pulses specific to a certain preset, e.g., $TSP_2$, for one image frame, and then transmitting pulses specific to a different preset, e.g., $TSP_3$, for the next image frame. The transducer may thus cycle through multiple presets, e.g., $TSP_4$ and $TSP_5$, dedicating one frame to each preset (represented by the diagonal arrow 309). Specifically, $TSP_1$ may be used to acquire images of the heart 302 at each of timepoints $t_{1-6}$ during one cardiac cycle, while $TSP_2$ may be used to acquire image $i_2$ at $t_2$ of another cardiac cycle, $TSP_3$ may be used to acquire image $i_3$ at $t_3$, $TSP_4$ is used to acquire image $i_4$ at $t_4$, and $TSP_5$ is used to acquire image is at $t_5$. After acquiring image is, the ultrasound transducer may re-initiate imaging using a fixed TSP. Any of $TSP_{S1-5}$ may be used for fixed imaging. In the example shown, the ultrasound transducer re-initiates fixed imaging using $TSP_5$, thus acquiring image $i_6$ at $t_6$. The ultrasound transducer may continue imaging using $TSP_5$ for a predetermined length of time, e.g., one or more additional cardiac cycles, or for any length of time desired.

As is evident in FIG. 3, constant use of $TSP_1$ across the entire cardiac cycle may be sub-optimal due to the unfocused, blurry images of the cardiac walls produced at several timepoints 306 using this setting. Embodiments herein may be arranged to avoid this problem by identifying the TSP which produces the best image of the heart 302 (or other object 105) at each timepoint. The example shown includes five presets, but greater or fewer presets may be implemented according to embodiments described herein. For example, a user may specify the number or type of presets to eliminate one or more presets if the eliminated presets are unlikely to be relevant for a given imaging operation.

In some examples, switching from one TSP to the next TSP may involve switching from one transmission pulse to another transmission pulse at a different spatial location. According to such examples, different lines may be sonicated with pulses from different TSPs at different frames. The system components used to implement such embodiments may be the same as shown, for example, in FIGS. 1 and 2.

Figure 4:
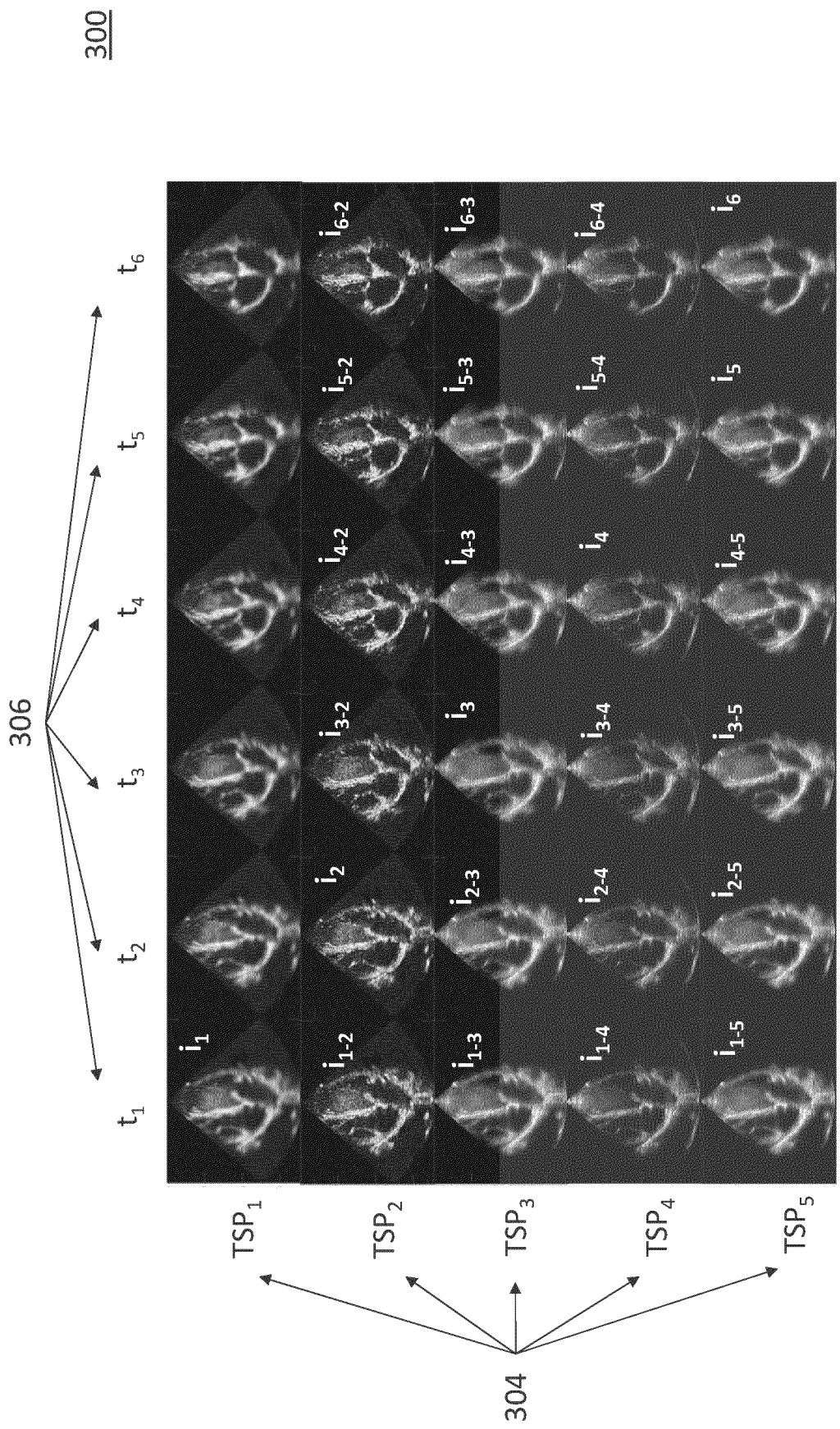
FIG. 4 is another schematic diagram of the image acquisition scheme of FIG. 3, showing the result of deep learning-based beamforming, according to embodiments of the present disclosure.

FIG. 4 is a schematic diagram of the image acquisition scheme 300 shown in FIG. 3 after the incorporation of images $i_{1-2}$-$i_{6-4}$ beamformed using one or more neural networks. As shown, the initially acquired images $i_{1-6}$, beamformed using DAS-based beamforming, are now accompanied by 19 additional images $i_{1-2}$-$i_{6-4}$ generated using neural network-based beamforming of the initial channel data acquired at each timepoint.

In the example shown, image $i_{1-2}$ is generated by performing neural network-based beamforming of the channel data used to acquire image $i_1$ at timepoint $t_1$, but in accordance with $TSP_2$ instead of the preset actually used to acquire the image dataset ($TSP_1$). Image $i_{1-3}$ is also generated by performing neural network-based beamforming of the channel data used to acquire image $i_1$, but in accordance with $TSP_3$. Likewise, image $i_{2-3}$ is generated by performing neural network-based beamforming of the channel data used to acquire image $i_2$, but in accordance with $TSP_3$. Accordingly, the missing images for each of the timepoints 306 (represented by each column of the matrix) and each of the TSPs 304 (represented by each row) may be populated using the channel data acquired using a certain TSP, but beamformed using one or more neural networks trained to map the channel data to beamformed signals corresponding to a different TSP, i.e., not the TSP used to acquire the original data.

Per-channel data may be saved and later processed, or transferred directly to a processing unit (e.g., FPGA GPU or CPU) for processing without being saved. All images generated in this manner, or at least a subset of images, may be displayed simultaneously for user review, thereby facilitating the selection of an optimal TSP, or multiple TSPs, for imaging a certain feature.

Figure 5:
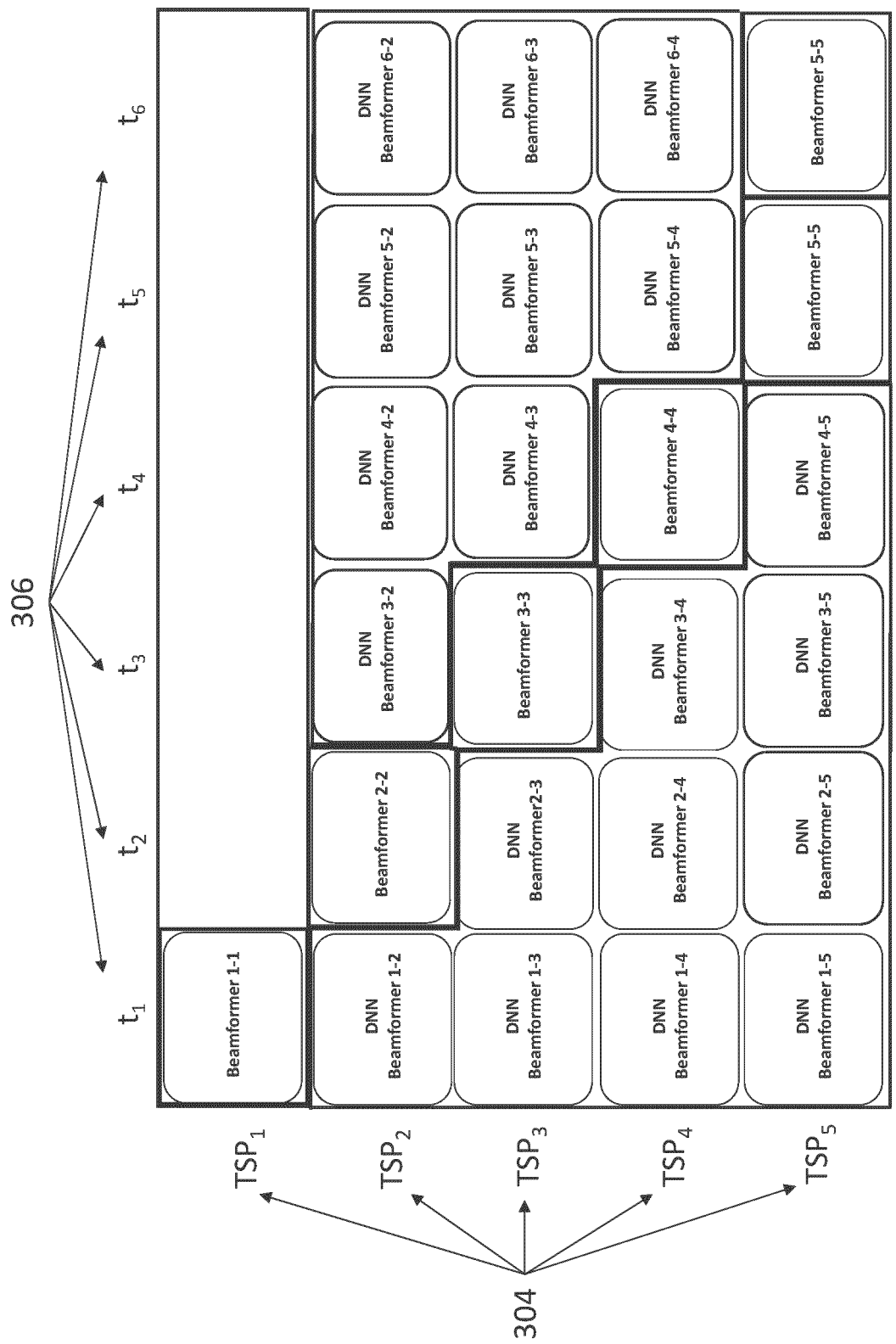
FIG. 5 is a schematic diagram of the beamformers that may be utilized to execute the image acquisition scheme of FIGS. 3 and 4, according to aspects of the present disclosure.

FIG. 5 is a schematic diagram of the beamformers 500 that may be utilized in accordance with the image acquisition scheme 300 shown in FIGS. 3 and 4. FIG. 5 shows the beamformers that may be used for applying each TSP at each timepoint. That is, the arrangement of beamformers shown in FIG. 5 does not represent a physical allocation of beamformers, but a conceptual arrangement consistent with image acquisition scheme 300. As shown, embodiments may utilize multiple hardware beamformers (Beamformers 1-1 through 5-5) to reconstruct images from multiple TSPs using DAS-based beamforming, thereby generating images $i_1$-$i_6$, each of which corresponds to the TSP used to acquire the initial channel data at each of the timepoints 306. The deep neural network beamformers (DNN Beamformers 1-2 through 6-4) may each be trained to beamform channel data acquired using an initial TSP into image data corresponding to a different TSP. For example, DNN Beamformer 1-2 is trained to use the per-channel data acquired using $TSP_1$ to form an image which appears as if it was acquired using $TSP_2$. DNN beamformer 1-2 is thus trained using input data acquired with $TSP_1$ and output data obtained via $TSP_2$. Each DNN beamformer may constitute a discrete layer of a multilayered network (e.g., machine learning network 142), or one of several individual neural networks. The number of DNN beamformers may vary. In some embodiments, for processing N number of TSP settings, N hardware beamformers will be required, and N(N−1) DNN beamformers will be required.

Figure 6:
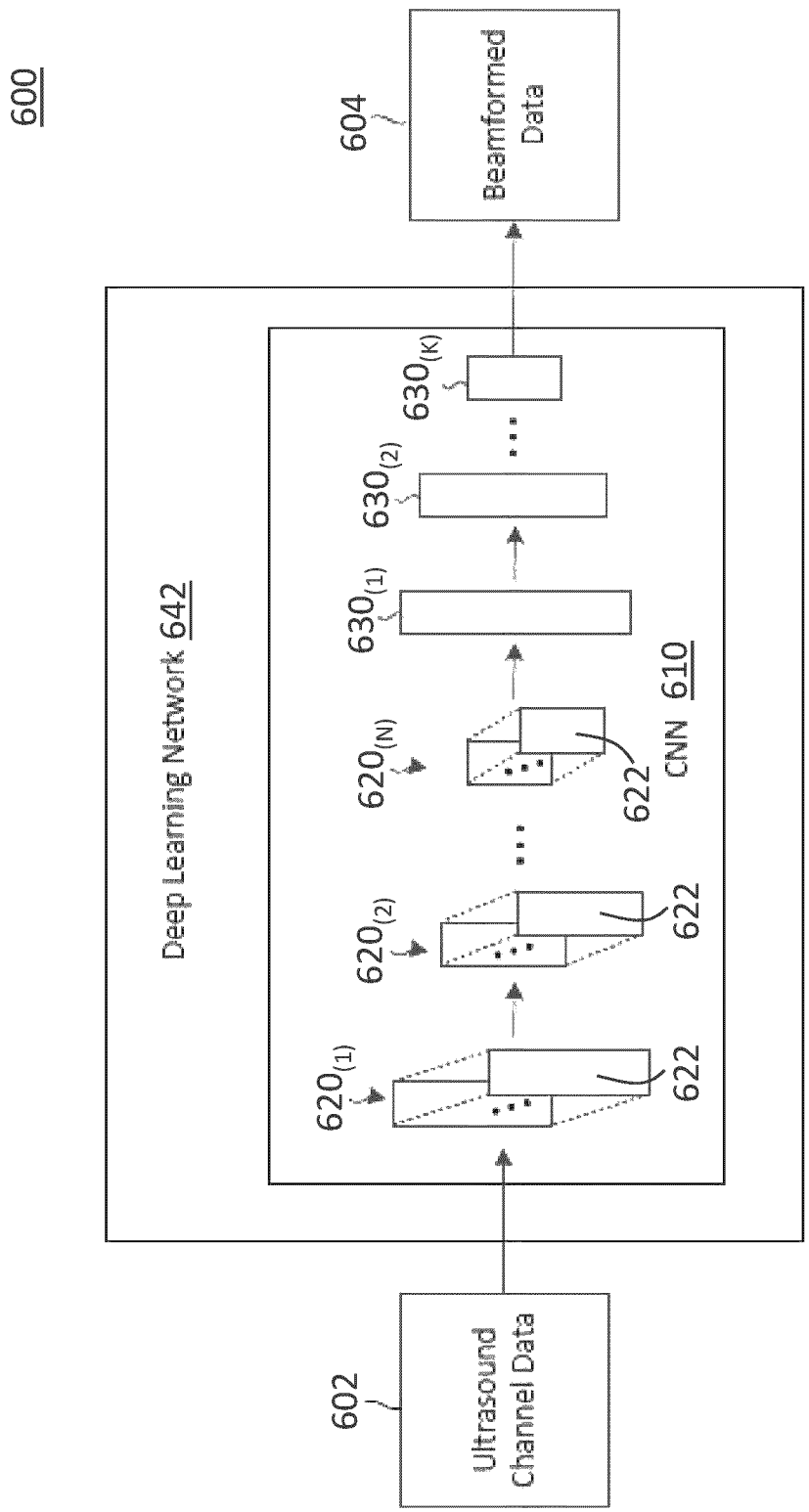
FIG. 6 is a schematic diagram illustrating a configuration of a deep learning network, according to aspects of the present disclosure.

FIG. 6 is a schematic diagram illustrating a configuration 600 of a deep learning network 642 (or deep neural network) that may be implemented to beamform channel data in accordance with one or more specific TSPs. The deep learning network 642 may include one or more CNNs 610. Each CNN 610 may operate on per-channel ultrasound channel data 602. The CNN 610 maps the per-channel ultrasound channel data 602 (acquired via one TSP) to beamformed data 604 (associated with a different TSP). In an example, the ultrasound channel data 602 may correspond to normalized, time-aligned ultrasound echo channel signals generated for example in accordance with the disclosures of U.S. 62/809,080 (filed Feb. 22, 2019), which is incorporated by reference in its entirety herein. The CNN 610 may provide per-channel pixel-based mapping of 2D data and/or 3D data to beamformed data.

The CNN 610 includes a set of N convolutional layers 620 followed by a set of K fully connected layers 630, where N and K may be any positive integers. The convolutional layers 620 are shown as $620_{(1)}$ to $620_{(N)}$. The fully connected layers 630 are shown as $630_{(1)}$ to $630_{(K)}$. In an example, the convolutional layers $620_{(1)}$ to $620_{(N)}$ and the fully connected layers $630_{(1)}$ to $630_{(K-1)}$ may utilize a Rectified Linear Unit (ReLU) non-linear activation function. The last output layer $630_{(K)}$ may utilize a linear activation function. Each convolutional layer 620 may include a set of filters 622 arranged to extract features from the ultrasound channel data 602. The values N and K and the sizes of the filters 622 in each convolutional layer 620 may vary depending on the embodiments. It should be noted that the CNN 610 may not necessarily include pooling layers that are commonly used to reduce the size of the convolutional layers. The exclusion of pooling layers allows all convolutions to contribute to the output of the CNN 610. Alternatively, the CNN 610 may include convolutional layers 620 only, or fully connected layers 630 only.

In an example, the ultrasound channel data 602 may include a 2D dataset spanning an x-dimension corresponding to receive channels (e.g., Channel(1) to Channel (M) of FIG. 2) and a y-dimension corresponding to imaging depths. The CNN 610 may include about five convolutional layers 620 (e.g., N=5) and about two fully connected layers 630 (e.g., K=2). The convolution layers 620 may include 2D convolutional kernels (e.g., the filters 622) spanning in the x and y dimensions. The 2D convolutional kernel size may vary depending on the embodiments. In some examples, the same 2D convolutional kernel size is used for all convolutional layers 620. In some examples, different 2D convolutional kernel sizes may be used for the convolutional layers 620. In some examples, the 2D convolutional kernel size may be dependent on the ultrasound transmission configuration used for collecting the ultrasound channel data 602. The first convolutional layer $620_{(1)}$ layer may include about sixty-four filters 622 or 2D convolutional kernels, or between 44 and 84 filters, the second convolutional layer $620_{(2)}$ layer may include about thirty-two filters 622, or between 20 and 44 filters, the third convolutional layer $620_{(3)}$ layer may include about sixteen filters 622, or between 8 and 24 filters, the fourth convolutional layer $620_{(4)}$ layer may include about eight filters 622, or between 4 and 12 filters, and the fifth convolutional layer $620_{(5)}$ layer may include about four filters 622, or between 2 and 6 filters. The first fully connected layer $630_{(1)}$ may have a size of about 32, or between 20 and 44, and the last fully connected layer $630_{(2)}$ may have a size of about 1, or between 1 and 3, 5, or 7. The output at the last fully connected layer $630_{(2)}$ corresponds to a single beamformed output sample or pixel.

In another example, the ultrasound channel data 602 may include a 3D dataset spanning an x-dimension corresponding to receive channels (e.g., Channel(1) to Channel (M) of FIG. 2), a y-dimension corresponding to imaging depths, and a z-dimension corresponding to transmit triggers or transmit events. The CNN 610 may include about six convolutional layers 620 (e.g., N=6) and about four fully connected layers 630 (e.g., K=4). The convolution layers 620 may include 3D convolutional kernels spanning in the x, y, and z dimensions. The 3D convolutional kernel size may vary depending on the embodiments. In some examples, the same 3D convolutional kernel size is used for all convolutional layers 620. In some examples, different 3D convolutional kernel size may be used for the convolutional layers 620. In some examples, the 3D convolutional kernel size may be dependent on the ultrasound transmission configuration used for collecting the ultrasound channel data 602. The first convolutional layer $620_{(1)}$ layer may include about sixty-four filters 622 or 3D convolutional kernels, or between 44 and 84 filters, the second convolutional layer $620_{(2)}$ layer may include about thirty-two filters 622, or between 20 and 44 filters, the third convolutional layer $620_{(3)}$ layer may include about sixteen filters 622, or between 8 and 24 filters, the fourth convolutional layer $620_{(4)}$ layer may include about eight filters 622, or between 4 and 12 filters, the fifth convolutional layer $620_{(5)}$ layer may include about four filters 622, or between 2 and 6 filters, and the sixth convolutional layer $620_{(6)}$ layer may include about two filters 622, or between 2 and 3, 5, or 7 filters. The first fully connected layer $630_{(1)}$ may have a size of about 32, or between 20 and 44, the second fully connected layer $630_{(2)}$ may have a size of about 16, or between 8 and 24, the third fully connected layer $630_{(3)}$ may have a size of about 8, or between 4 and 12, and the last fully connected layer $630_{(4)}$ may have a size of about 1, or between 1 and 3, 5, or 7. The output at the last fully connected layer $630_{(4)}$ corresponds to a single beamformed output sample or pixel.

In some examples, the CNN 610 may include a flattening layer at the output of the last convolutional layer $620_{(N)}$ to convert the convolutional part of the CNN 610 into a 1D feature vector for the subsequent fully connected layers 630. In some examples, the convolutional layers 620 may include zero padding such that the input and output size of the convolution or filter 622 are the same. In some examples, the CNN 610 may include an additional layer before the first convolutional layer $620_{(1)}$ for normalization, and an additional layer after the last fully connected layer $630_{(K)}$ for denormalization, for example as described in U.S. 62/809,080. Thus, the CNN 610 may be applied without explicitly normalizing the time-align per-channel ultrasound echo signals and without explicitly de-normalizing the output of the CNN 610.

Figure 7:
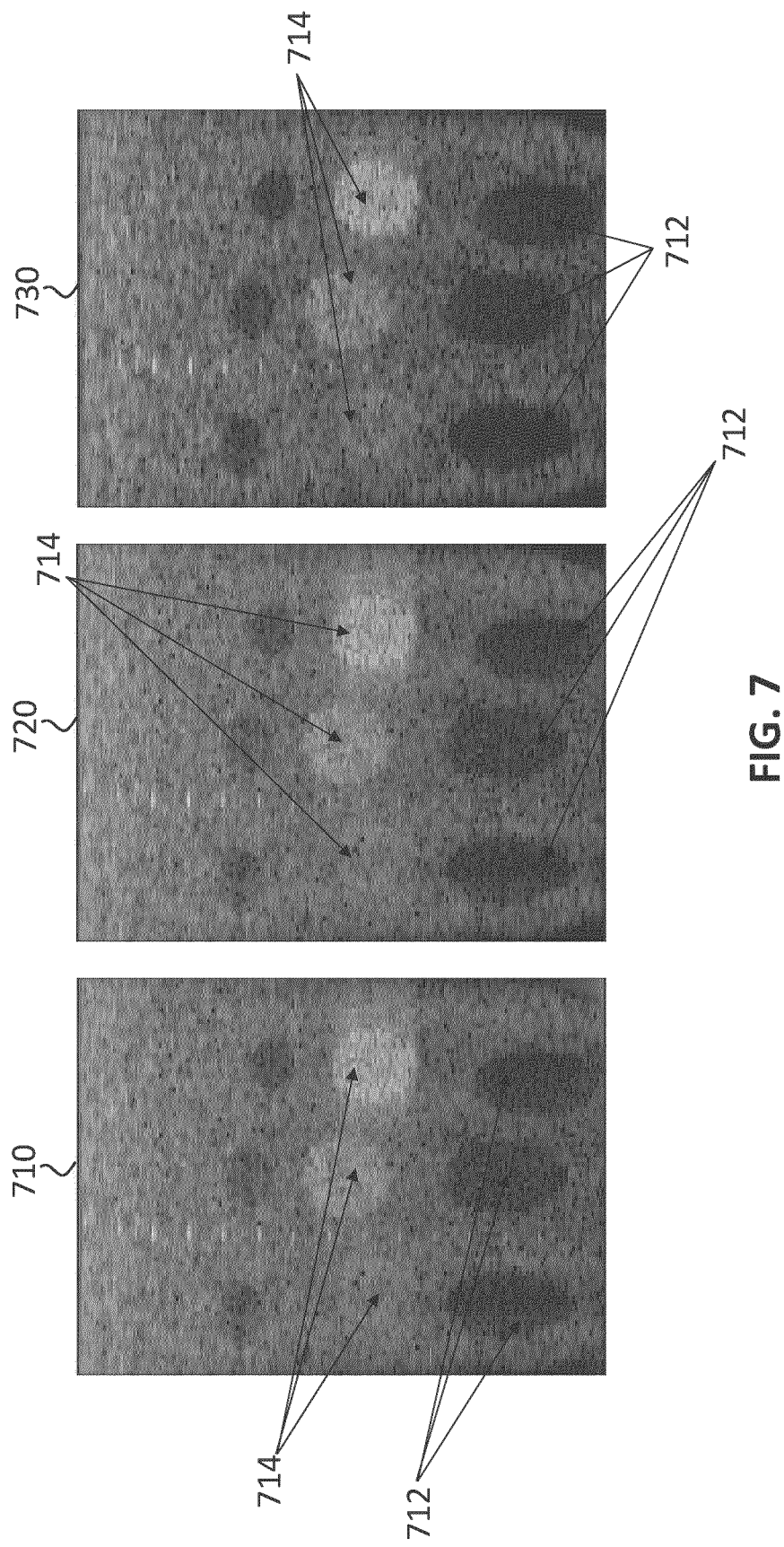
FIG. 7 illustrates ultrasound images generated from DAS-based beamforming and deep learning-based beamforming, according to aspects of the present disclosure.

FIG. 7 shows ultrasound images generated separately using DAS-based beamforming or deep learning-based beamforming, according to aspects of the present invention. The ultrasound images 710, 720 and 730 are all generated from the same set of per-channel ultrasound echo signals acquired from a simulated phantom, each showing dark cysts 712 and brighter lesions 714. The ultrasound image 710 is generated using a conventional DAS-based beamformer (e.g., the beamformer 114) to beamform the acquired per-channel ultrasound echo signals, whereas the ultrasound image 720 is generated by applying a deep learning network (e.g., the deep learning network 642 trained using the scheme 800 shown in FIG. 8) to map per-channel echo signals to beamformed data. Both ultrasound images 710 and 720 are formed in accordance with the same TSP, using five diverging wave transmissions and compounding. As shown, the ultrasound image 720 formed via deep learning-based beamforming appears nearly identical to the ultrasound image 710 formed via DAS-based beamforming.

The ultrasound image 730 is generated using a deep learning network trained to receive aligned data from five transmits and output values beamformed by coherently compounding 51 transmits. The ultrasound image 730 shows reduced clutter in the dark cysts 712 and improved contrast for the brighter lesions 714. Accordingly, deep learning networks may be arranged to not only beamform channel data in a predictive manner that mimics DAS-based beamforming, but to beamform channel data in a predictive manner that improves image resolution and overall quality.

Figure 8:
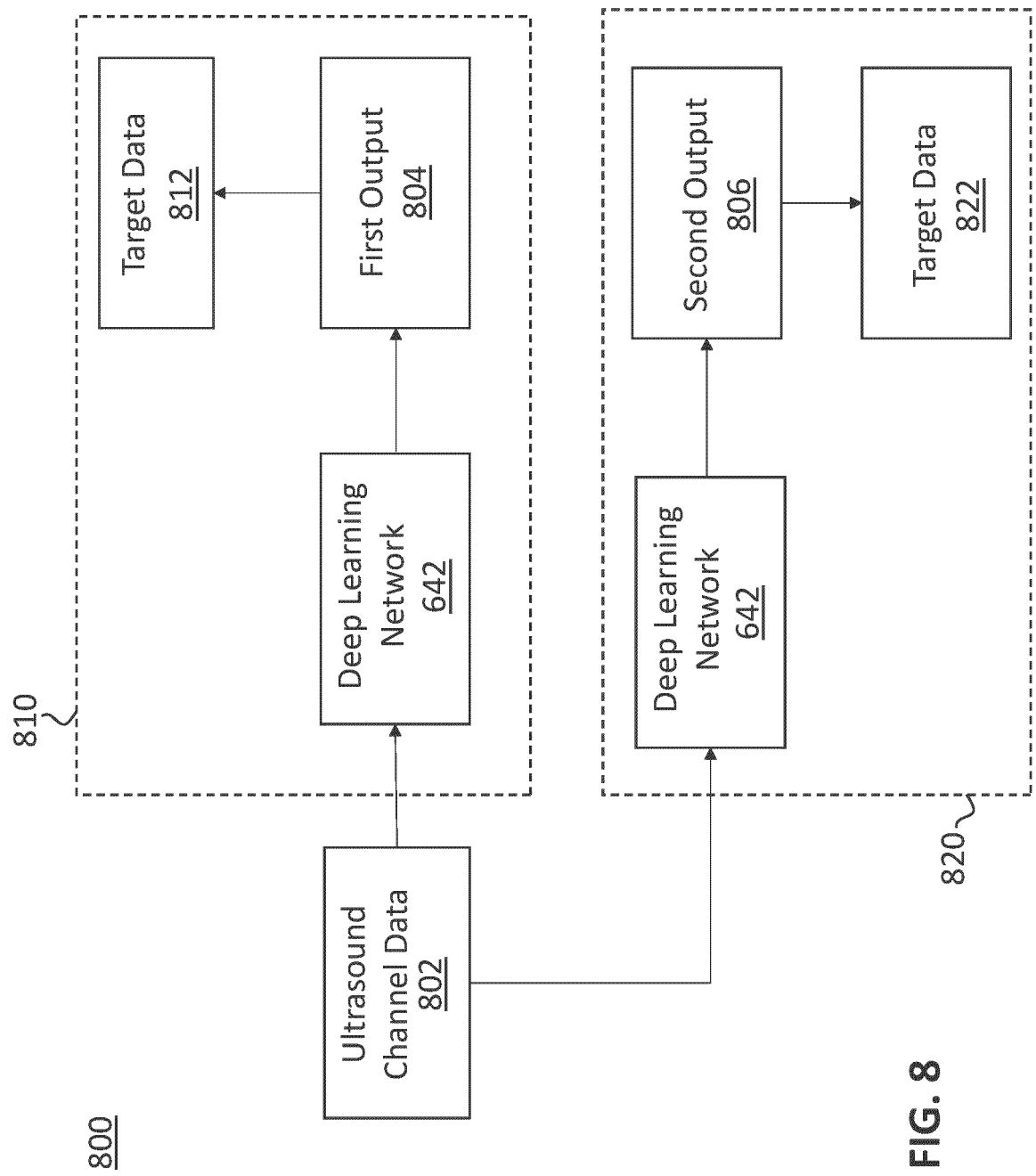
FIG. 8 is a schematic diagram illustrating a deep learning network training scheme, according to aspects of the present disclosure.

FIG. 8 is a schematic diagram illustrating a deep learning network training scheme 800, according to aspects of the present disclosure. The scheme 800 may be implemented by a computer system, such as the host 130 shown in FIG. 1 and/or the processor 1100 shown in FIG. 11. The scheme 800 may be employed to train the deep learning network 642, or multiple neural networks, for ultrasound beamforming. The scheme 800 trains the deep learning network 642 to predict or imitate beamformed data obtained from a transducer utilizing a different TSP than a transducer in use.

The scheme 800 may train the deep learning network 642 in two stages 810 and 820. Both stages may involve the use of ultrasound channel data 802 as the training input, which the deep learning network 642 transforms into a first output 804 in the first stage 810 and a second output 806 in the second stage 820. In the first stage 810, the scheme 800 trains the deep learning network 642 using an input-output pair, where the input includes ultrasound channel data 802 and the output includes target beamformed data 812. The ultrasound channel data 802 may comprise normalized, time-aligned ultrasound echo channel signals. The ultrasound channel data 802 may be acquired from a transducer array (e.g., the transducer 112), and the ultrasound channel data 802 may correspond to ultrasound echo responses received from a certain subject (e.g., the object 105). The ultrasound channel data 802 may be a 2D dataset with an x-dimension corresponding to receive channels and a y-dimension corresponding to imaging depths.

The target data 812 may correspond to beamformed data generated from the ultrasound channel data 802 using a DAS-based beamformer (e.g., the beamformer 114). The target data 812 may also be normalized so that the training does not have to learn amplitude mapping.

During training, the deep learning network 642 may be applied to the ultrasound channel data 802 using forward propagation to produce first output 804 (e.g., beamformed data). The coefficients of the filters 622 in the convolutional layers 620 and the weightings in the fully connected layers 630 may be adjusted using backward propagation to minimize the error between the first output 804 and the target output 812. In some embodiments, the error function or the loss function may be a mean-square-error (MSE) function or any other suitable error measure function. In other words, the scheme 800 trains the deep learning network 642 to approximate the beamforming provided by the beamformer 114. The training or the adjusting of the coefficients for the filters 622 may be repeated for multiple input-output pairs. The first stage 810 functions as an initialization of filter coefficients and/or weights in the deep learning network 642.

In some embodiments, a perceptual loss function may be used to evaluate and improve the performance of the deep learning network 642. According to such embodiments, the loss function may utilize a pre-trained classifier network, which includes higher level features used to compute a loss value, in addition to the neural networks used to perform beamforming described herein, e.g., the deep learning network 642. Either the final output of such a loss network (not shown) or outputs at higher feature layers may be used to define the loss function. In an example, a network may be trained to distinguish between images acquired using one TSP, e.g., defined by five diverging wave transmits, versus images acquired via another TSP, e.g., defined by 51 diverging wave transmits. The loss network may then be used to calculate the loss term for the deep learning network 642 to map per-channel data of five transmits to beamsum values of 51 transmits, for example. A loss term generated via perceptual loss may be very large for images having a low probability of belonging to the target class, e.g., the target TSP. As the number of features resembling the target loss are increased during training, the loss value shrinks. Such a loss term may be utilized alone or in conjunction with MSE to evaluate and improve the performance of the deep learning network 642.

In addition or alternatively, an adversarial loss function may be used. Like perceptual loss, an adversarial loss approach may utilize two networks: one network for beamforming and one network for calculating the loss on the beamforming network, e.g., deep learning network 642. The loss network may be trained alongside the beamforming network during the training process, e.g., while the scheme 800 is utilized.

In the subsequent stage 820, the scheme 800 uses the filter coefficients and/or weights obtained for the deep learning network 642 from the first stage 810 as a start and continues with the training. The scheme 800 trains the deep learning network 642 using an input-output pair, where the input includes ultrasound channel data 802 and the output includes beamformed target data 822. The target data 822 may correspond to beamformed data of the same subject generated from a transducer applying a different TSP, such that the deep learning network 642 learns to map features from per-channel data to the image pixel value of a different image acquisition setting, for example a different number of diverging transmits for fast imaging, as shown above in FIG. 7. The target data 822 is normalized data.

Continuing with the examples shown in FIGS. 3-5, the target data 812 may be generated for $TSP_1$ and the target data 822 may be generated for a transducer applying $TSP_5$. Similar to the first stage 820, the deep learning network 642 is trained by applying the ultrasound channel data 802 using forward propagation to produce an output 806. The coefficients of the filters 622 in the convolutional layers 620 and the weightings in the fully connected layers 630 may be adjusted using backward propagation to minimize the error between the output 806 and the target output 822. The training or the adjusting of the coefficients for the filters 622 may be repeated for multiple input-output pairs. While the scheme 800 utilizes two stages of training, in some embodiments, the scheme 800 may perform the second stage 820 of training without performing the first stage 810 of the training.

The training scheme 800 may use any suitable combination of simulation data generated offline, data acquired from a patient in a clinical setting, and data acquired from a phantom in a test setup to train the deep learning network 642. In some examples, using actual data acquired from an ultrasound system (e.g., the systems 100 and 200) instead of or at least in addition to simulation data as input-output data pairs, may be advantageous due to the oversimplification of physical phenomena that may result from using simulation data. By at least complementing simulation data with real data from phantom and ex vivo imaging, the deep learning network 642 may be trained to accurately suppress clutters from noise sources, such as acoustic noise, thermal noise, electronic noise, aberration, and/or reverberation, that are introduced due to poor acoustic conditions and cannot be addressed along the signal paths of the ultrasound system (e.g., the systems 100 and/or 200). The same phantom material or ex vivo model may be imaged using multiple different TSPs. The raw data may be saved as the input data for each TSP and the output data may be saved as the beamsum value for each corresponding TSP. In vivo models may also be used as a data source. Data collection from such models may require imaging with gated sequences (e.g., cardiac gating, respiratory gating, etc.) to synchronize two sets of images acquired at different times, which are then paired for training.

As can be observed, the scheme 800 trains the deep learning network 642 to map per-channel ultrasound echo signals to beamformed data corresponding to a different TSP than the TSP of the transducer used for collecting the ultrasound echo channel signals. Accordingly, the deep learning network 642 may provide more focused or less focused image features in the final reconstructed images than a conventional DAS-based beamformer (e.g., the beamformed 114). Less focused images produced by a given TSP reduce the likelihood of a user selecting that TSP for continued examination.

Figure 9:
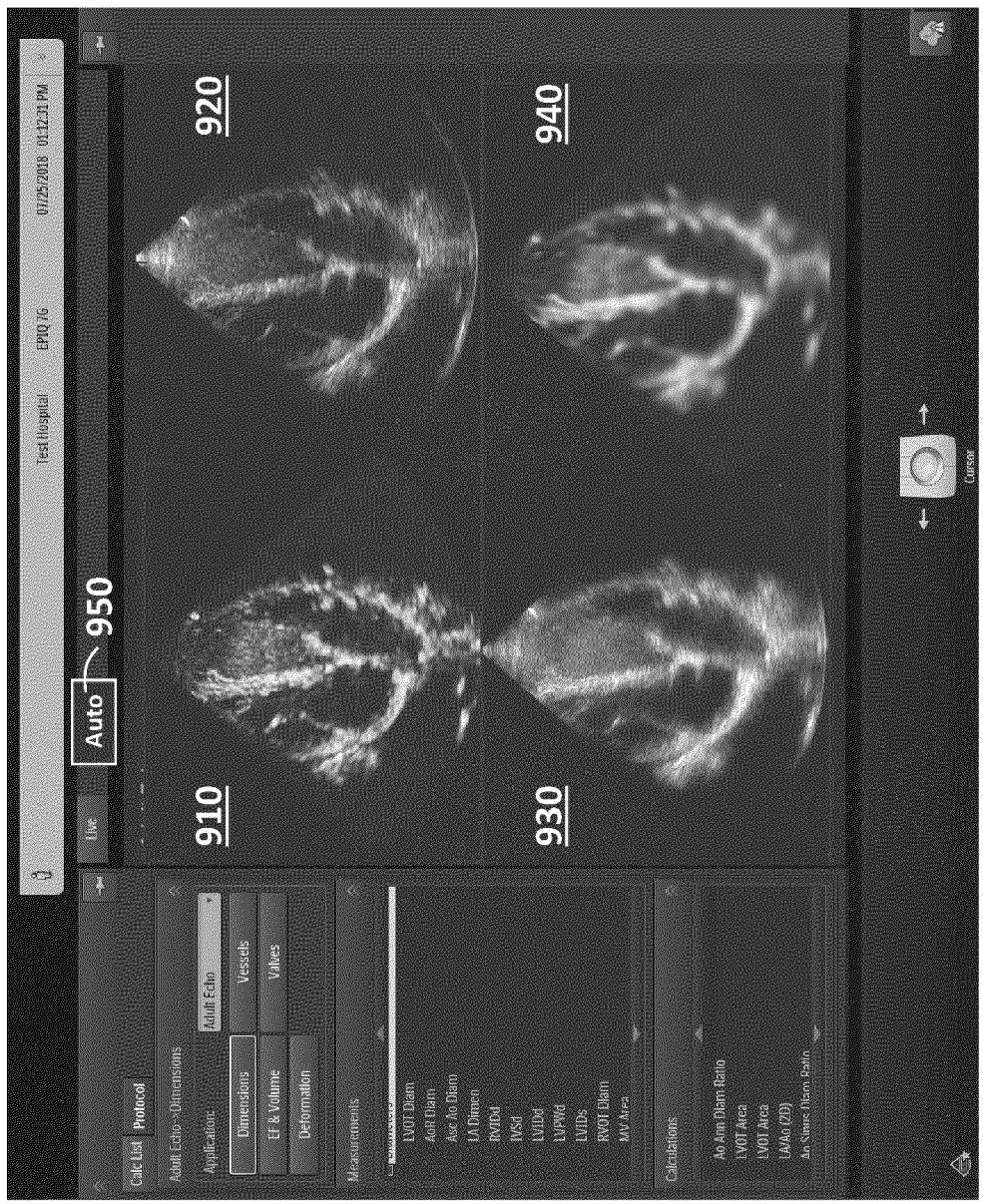
FIG. 9 illustrates a display arranged to show ultrasound images generated using deep learning-based beamforming, according to aspects of the present disclosure.

FIG. 9 illustrates a display 900, e.g., user interface, showing ultrasound images generated from deep learning-based beamforming, according to aspects of the present disclosure. The data used to acquire the ultrasound images 910, 920, 930 and 940 are acquired from an in-vivo scan of a patient's heart. The ultrasound images 910, 920, 930 and 940 may be generated by applying the deep learning network 642 to map per-channel ultrasound echo signals with beamformed data corresponding to four different TSPs. The four images 910, 920, 930 and 940 shown on the display 900 may be selected by a user based on a visual analysis of images generated via DAS-based beamforming and deep learning-based beamforming over the course of a cardiac cycle. The images 910, 920, 930 and 940 may be displayed in real time, e.g., during a scan, or in a review mode as recorded cine-loops. As further shown, the display 900 may include a button 950 or selectable indicator arranged to initialize an automatic acquisition mode ("Auto") comprising the scheme 300 shown in FIGS. 3 and 4.

Figure 10:
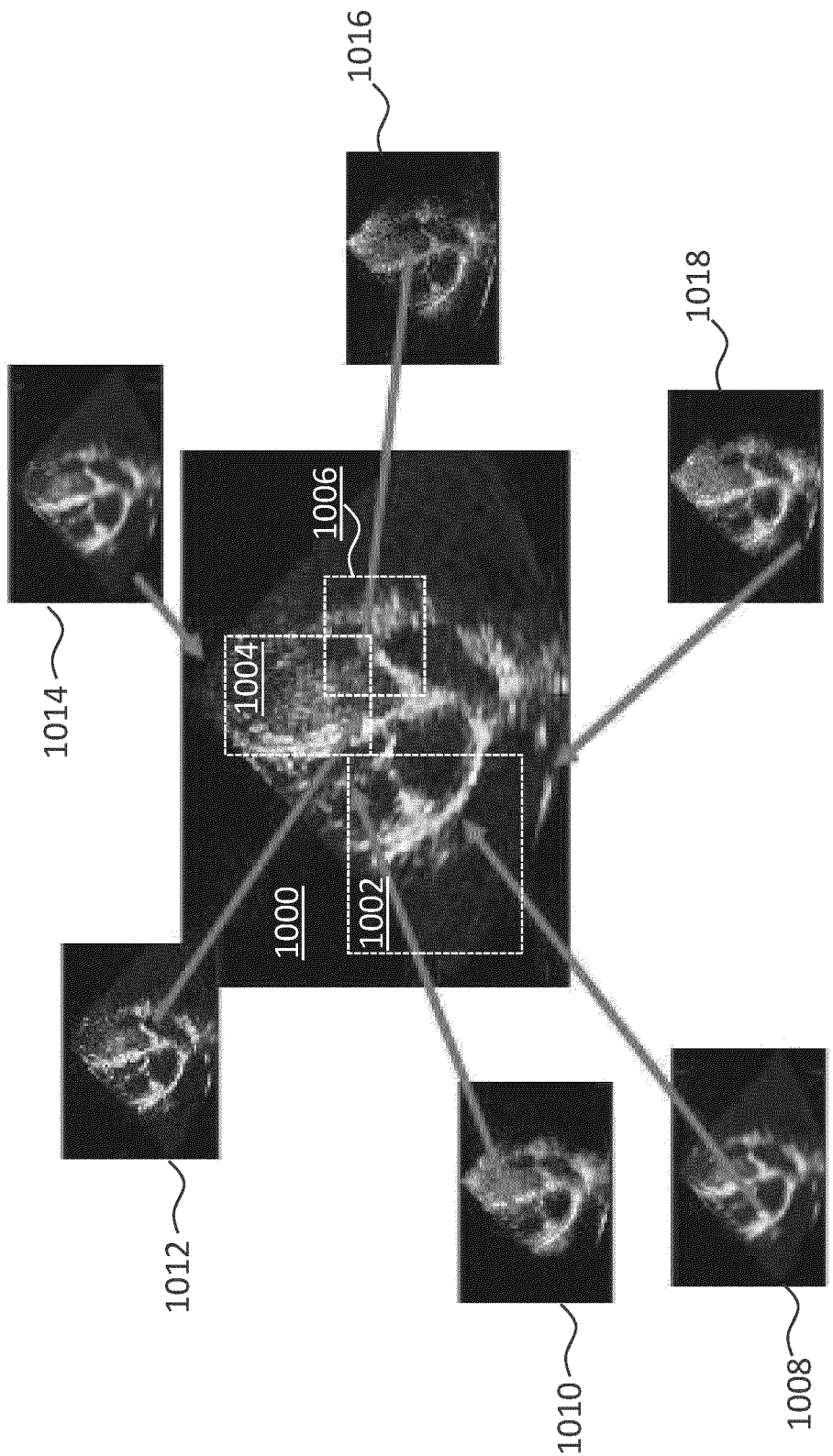
FIG. 10 illustrates a composite ultrasound image generated from deep learning-based beamforming, according to aspects of the present disclosure.

FIG. 10 illustrates an example of a composite image 1000 of a heart generated from deep learning-based beamforming, according to aspects of the present disclosure. The composite image 1000 may be generated using a processor circuit (e.g., display processor circuit 134) arranged to blend weighted image features acquired using various TSPs. One or more bounding boxes 1002, 1004, 1006 may be utilized to generate the composite image 1000 according to certain embodiments. The composite image 1000 may comprise a combination of optimized image segments generated using multiple TSPs, for example including images of smooth pericardium texture 1008, improved delineation of weak endocardium 1010, a high resolution valve 1012, a clean apex 1014, reduced clutter in one or more heart chambers 1016, and increased penetration 1018.

To form the composite image 1000, a user may select and/or segment portions of individual images generated from different TSPs, such as those depicted in FIG. 4, and adjust the weight of such TSP-specific segments for preferential blending within the composite image 1000. The selected/segmented portion of each image may be tracked (e.g., using a separate neural network or a speckle tracking algorithm), and the desired blending weight applied to the image portion for each frame within a cine-loop. The final composite image 1000 includes greater input from image segments assigned a greater weight. In an example, the final composite image may be formulated as $I_c = \Sigma w_i + I_i$ for each pixel, where "i" represents the TSP number, "$I_i$" represents the image beamformed for the I'th TSP, "$I_c$" represents the final composite image, and "w" represents the weight for each TSP used in the blending process. In some examples, the composite image may be normalized by dividing by the sum of all $w_i$ terms to obtain a distortionless compounded image.

In addition to user-defined weighting of one or more features imaged using different TSPs, systems may include an additional classifier neural network trained using high quality and low quality images. Such a network may be arranged to optimize the feature weights such that the final composite image has the highest possibility of being classified as a high quality image.

In yet additional embodiments, a detection algorithm may be utilized by the ultrasound system (e.g., system 100) to eliminate the need for manual selection of one or more image portions or segments. The detection algorithm may be arranged to position the bounding boxes 1002, 1004, 1006 around different anatomical structures, such as individual heart chambers, valves, septum, pericardium, etc. Different TSP settings may then be applied to each region-of-interest defined by a specific bounding box.

Generally, aspects of the present disclosure describe using a machine learning network to replace one or more conventional ultrasound image processing steps, such as beamforming, that are required to generate conventional ultrasound images. The machine learning network is applied to the raw channel data obtained by the ultrasound transducer, rather than one or more of the conventional image processing steps being carried out on the raw channel data (e.g., beamforming and/or compounding of multiple transmits). The machine learning network is trained using a plurality of target beamformed data. Application of the machine learning network to the raw channel data results in modified data. A processor circuit generates the ultrasound image using the modified data, which includes a trait of the target images (e.g., anatomical structure, speckle, etc.). While the disclosed embodiments are described in the context of mapping ultrasound echo channel data RF data to beamformed data using deep learning, in some embodiments, similar deep learning techniques may be applied to map ultrasound echo channel data in an intermediate frequency (IF) or baseband (BB) to beamformed data.

Figure 11:
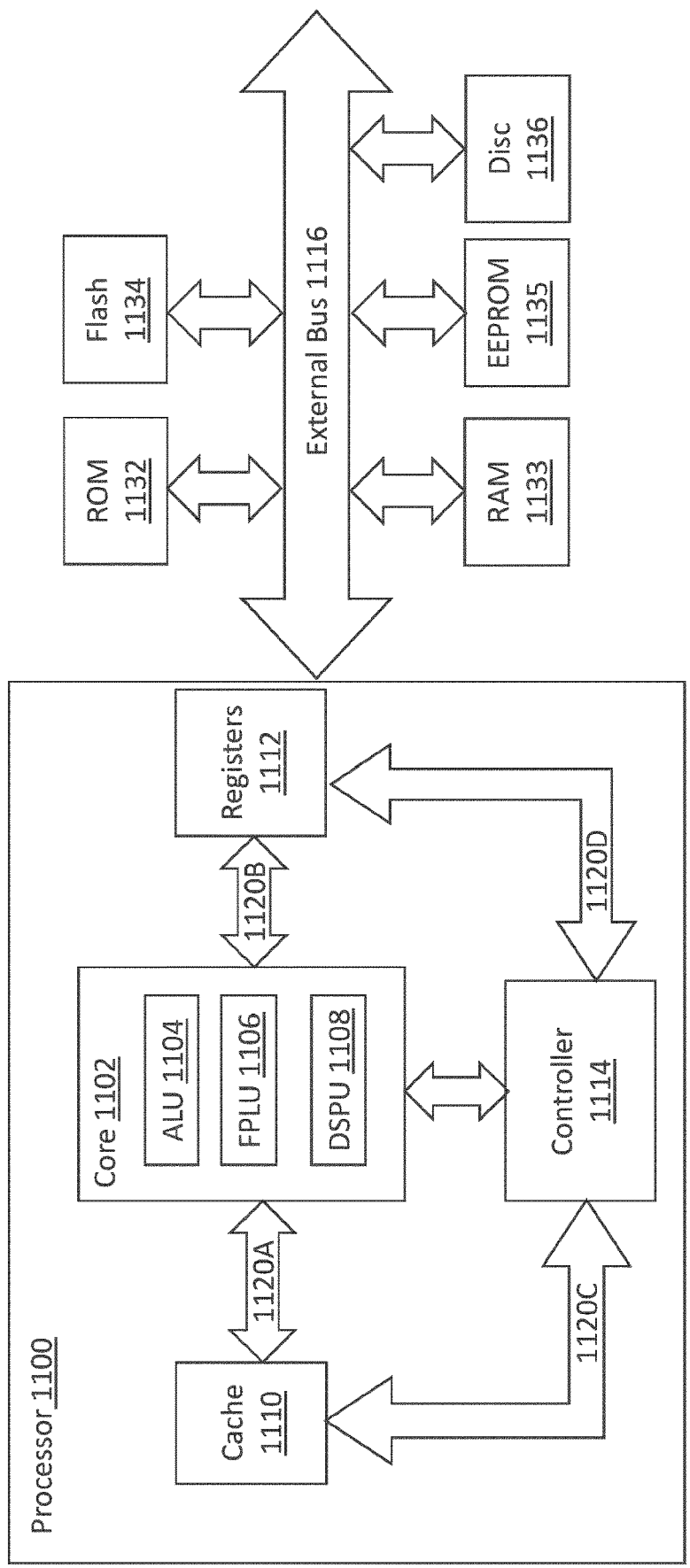
FIG. 11 is a schematic diagram of a processor circuit, according to embodiments of the present disclosure.

FIG. 11 is a block diagram illustrating an example processor 1100 according to embodiments of the disclosure. Processor 1100 may be used to implement one or more processors described herein, for example, probe processor circuit 116 or display processor circuit 134 shown in FIG. 1. Processor 1100 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 1100 may include one or more cores 1102. The core 1102 may include one or more arithmetic logic units (ALU) 1104. In some embodiments, the core 1102 may include a floating point logic unit (FPLU) 1106 and/or a digital signal processing unit (DSPU) 1108 in addition to or instead of the ALU 1104.

The processor 1100 may include one or more registers 1112 communicatively coupled to the core 1102. The registers 1112 may be implemented using dedicated logic gate circuits (e.g., flip-flops) and/or any memory technology. In some embodiments the registers 1112 may be implemented using static memory. The register may provide data, instructions and addresses to the core 1102.

In some embodiments, processor 1100 may include one or more levels of cache memory 1110 communicatively coupled to the core 1102. The cache memory 1110 may provide computer-readable instructions to the core 1102 for execution. The cache memory 1110 may provide data for processing by the core 1102. In some embodiments, the computer-readable instructions may have been provided to the cache memory 1110 by a local memory, for example, local memory attached to the external bus 1116. The cache memory 1110 may be implemented with any suitable cache memory type, for example, metal-oxide semiconductor (MOS) memory such as static random access memory (SRAM), dynamic random access memory (DRAM), and/or any other suitable memory technology.

The processor 1100 may include a controller 1114, which may control input to the processor 1100 from other processors and/or components included in a system (e.g., communication interface 136 shown in FIG. 1) and/or outputs from the processor 1100 to other processors and/or components included in the system (e.g., display 132 shown in FIG. 1). Controller 1114 may control the data paths in the ALU 1104, FPLU 1106 and/or DSPU 1108. Controller 1114 may be implemented as one or more state machines, data paths and/or dedicated control logic. The gates of controller 1114 may be implemented as standalone gates, FPGA, ASIC or any other suitable technology.

The registers 1112 and the cache 1110 may communicate with controller 1114 and core 1102 via internal connections 1120A, 1120B, 1120C and 1120D. Internal connections may implemented as a bus, multiplexor, crossbar switch, and/or any other suitable connection technology.

Inputs and outputs for the processor 1100 may be provided via a bus 1116, which may include one or more conductive lines. The bus 1116 may be communicatively coupled to one or more components of processor 1100, for example the controller 1114, cache 1110, and/or register 1112. The bus 1116 may be coupled to one or more components of the system, such as components communication interface 136 mentioned previously.

The bus 1116 may be coupled to one or more external memories. The external memories may include Read Only Memory (ROM) 1132. ROM 1132 may be a masked ROM, Electronically Programmable Read Only Memory (EPROM) or any other suitable technology. The external memory may include Random Access Memory (RAM) 1133. RAM 1133 may be a static RAM, battery backed up static RAM, Dynamic RAM (DRAM) or any other suitable technology. The external memory may include Electrically Erasable Programmable Read Only Memory (EEPROM) 1135. The external memory may include Flash memory 1134. The External memory may include a magnetic storage device such as disc 1136. In some embodiments, the external memories may be included in a system, such as ultrasound imaging system 100 shown in FIG. 1.

Figure 12:
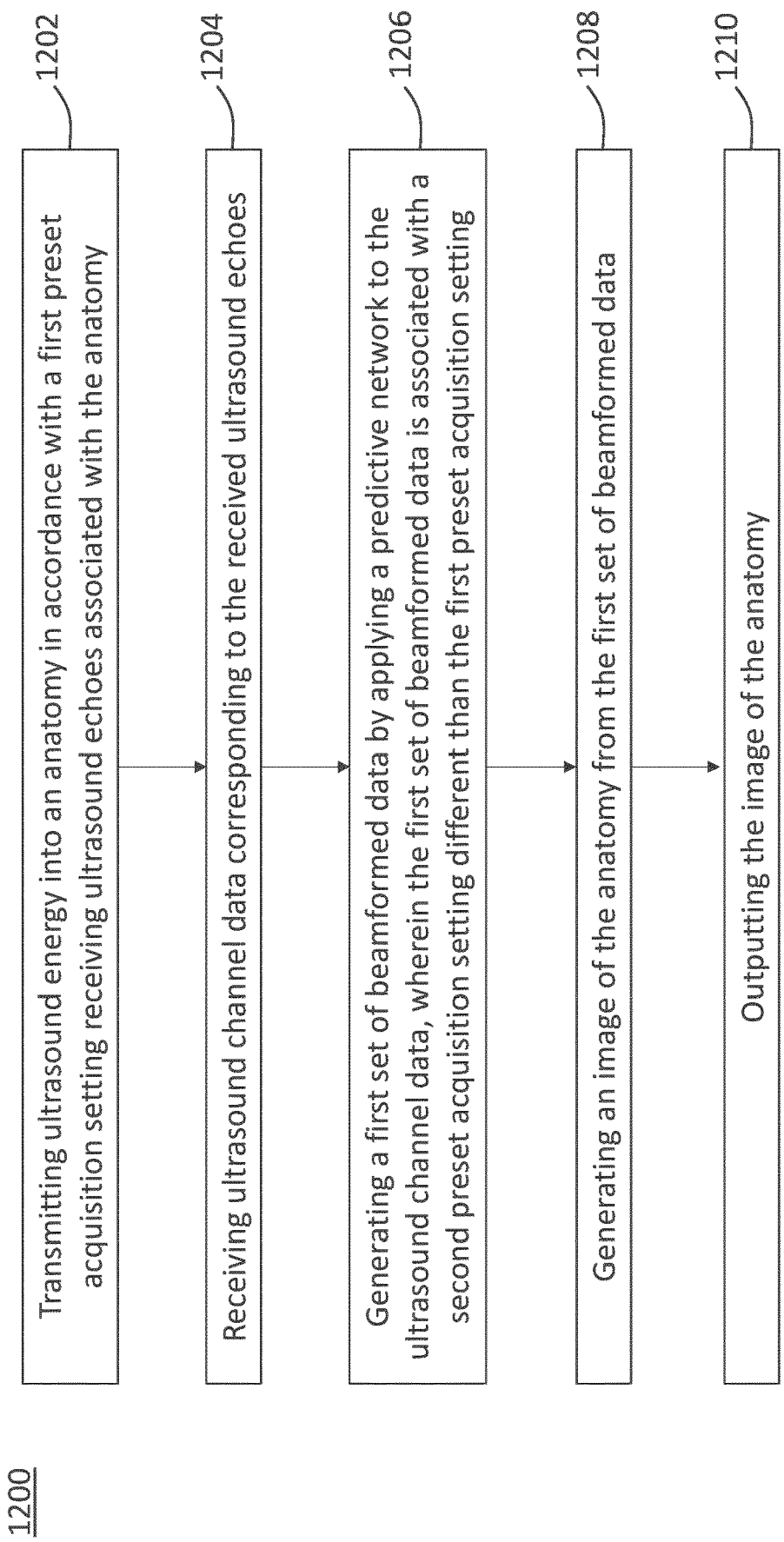
FIG. 12 is a flow diagram of a deep learning-based ultrasound imaging method, according to aspects of the present disclosure.

FIG. 12 is a flow diagram of a deep learning-base ultrasound imaging method 1200, according to aspects of the present disclosure. Steps of the method 1200 may be executed by the system 100 and/or 200 for example, by a processor such as the processor circuits 116, 134, or the processor 1160, processor circuit such as the processor circuit 1100, and/or other suitable component such as the probe 110 and/or the host 130. As illustrated, the method 1200 includes a number of enumerated steps, but embodiments of the method 1200 may include additional steps before, after, and in between the enumerated steps. In some embodiments, one or more of the enumerated steps may be omitted or performed in a different order.

At step 1202, the method 1200 involves "transmitting ultrasound energy into an anatomy in accordance with a first preset acquisition setting receiving ultrasound echoes associated with the anatomy."

At step 1204, the method 1200 involves "receiving ultrasound channel data corresponding to the received ultrasound echoes."

At step 1206, the method 1200 involves "generating a first set of beamformed data by applying a predictive network to the ultrasound channel data, wherein the first set of beamformed data is associated with a second preset acquisition setting different than the first preset acquisition setting."

At step 1208, the method 1200 involves "generating an image of the anatomy from the first set of beamformed data."

At step 1210, the method 1200 involves "outputting the image of the anatomy."

Aspects of the present disclosure may provide several benefits. Further, the use of the deep learning network may provide a computational cost advantage compared to conventional DAS-based beamformer (e.g., the beamformer 114) since operations in the inference stage of the deep learning network are mostly convolutions (e.g., multiply-adds) and matrix multiplications.

Persons skilled in the art will recognize that the apparatus, systems, and methods described above may be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, substitution and any combination of embodiments is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
   an array of acoustic elements,
     wherein the array of acoustic elements is configured to transmit ultrasound energy into an anatomy in accordance with a first preset acquisition setting,
     wherein the array of acoustic elements is configured to receive ultrasound echoes associated with the anatomy; and
   a processor circuit, wherein the processor circuit is in communication with the array of acoustic elements,
     wherein the processor circuit is configured to receive ultrasound channel data corresponding to the ultrasound echoes received from the array of acoustic elements,
     wherein the processor circuit is configured to generate a first set of beamformed data,
     wherein the beamformed data is generated by applying a predictive network to the ultrasound channel data,
     wherein the first set of beamformed data is associated with a second preset acquisition setting,
     wherein the second preset acquisition setting is different than the first preset acquisition setting,
     wherein the processor circuit is configured to generate an image of the anatomy from the first set of beamformed data, and
     wherein the processor circuit is configured to output the image of the anatomy to a display.

2. The system of claim 1,
   wherein the processor circuit is configured to generate a second set of beamformed data by applying the predictive network to the ultrasound channel data,
   wherein the second set of beamformed data is associated with a third preset acquisition setting,
   wherein the third preset acquisition setting is different than the first preset acquisition setting and the second preset acquisition setting.

3. The system of claim 2, wherein the processor circuit is further configured to process the channel data for generating the second set of beamformed data in parallel with the first set of beamformed data.

4. The system of claim 3,
   wherein the predictive network comprises a first neural network and a second neural network,
   wherein the first neural network is arranged in parallel to the second neural network,
   wherein the first neural network and the second neural network are arranged to output the first and second sets of beamformed data, respectively.

5. The system of claim 1, wherein the first and second preset acquisition settings are each applied for a single acquisition frame.

6. The system of claim 2,
   wherein the processor circuit is configured to generate an image of the anatomy from the second set of beamformed data,
     wherein the processor circuit is configured to output the image of the anatomy from the second set of beamformed data simultaneously with the image of the anatomy from the first set of beamformed data.

7. The system of claim 1,
   wherein the predictive network is trained by providing test ultrasound channel data,
   wherein the test ultrasound channel data is generated based on the first preset acquisition setting and a first target beamformed data generated based on the second preset acquisition setting; and wherein the predictive network is trained by training the predictive network to produce the first target beamformed data from the test ultrasound channel data.

8. The system of claim 7,
   wherein the predictive network is trained by providing second target beamformed data, wherein the second target beamformed data generated based on the first preset acquisition setting; and
   wherein the predictive network is trained to produce the second target beamformed data from the test ultrasound channel data before training the predictive network to produce the first target beamformed data.

9. The system of claim 1, wherein the array of acoustic elements includes a one-dimensional array of acoustic elements.

10. The system of claim 1, wherein the array of acoustic elements includes a two-dimensional array of acoustic elements.

11. A method of ultrasound imaging, comprising:
    transmitting ultrasound energy into an anatomy,
      wherein the ultrasound energy is transmitted in accordance with a first preset acquisition setting;
    receiving ultrasound echoes associated with the anatomy;
    receiving ultrasound channel data,
      wherein the ultrasound channel data corresponds to the received ultrasound echoes;
    generating a first set of beamformed data,
      wherein the first set of beamformed data is generated by applying a predictive network to the ultrasound channel data,
      wherein the first set of beamformed data is associated with a second preset acquisition setting,
      wherein the second preset acquisition setting is different than the first preset acquisition setting;
    generating an image of the anatomy;
      wherein the image is generated from the first set of beamformed data; and
    outputting the image of the anatomy.

12. The method of claim 11, further comprising generating a second set of beamformed data, wherein the second set of beamformed data is generated by applying the predictive network to the ultrasound channel data, wherein the second set of beamformed data is associated with a third preset acquisition setting, wherein the third acquisition setting is different than the first preset acquisition setting and the second acquisition setting.

13. The method of claim 12, further comprising processing the channel data for generating the second set of beamformed data in parallel with the first set of beamformed data.

14. The method of claim 13, wherein the predictive network comprises a first neural network and a second neural network, wherein the first neural network is arranged in parallel to the second neural network;

wherein the first neural network and the second neural network are arranged to output the first and second sets of beamformed data, respectively.

15. The method of claim 11, wherein the first and second preset acquisition settings are each applied for a single acquisition frame.

16. The method of claim 12, further comprising:

generating an image of the anatomy from the second set of beamformed data; and outputting the image of the anatomy from the second set of beamformed data, wherein the image of the anatomy from the second set of beamformed data is output simultaneously with the image of the anatomy from the first set of beamformed data.

17. The method of claim 11, further comprising training the predictive network, wherein the training comprises:

providing test ultrasound channel data;

wherein the test ultrasound channel data is generated based on the first preset acquisition setting and a first target beamformed data generated based on the second preset acquisition setting; and training the predictive network to produce the first target beamformed data from the test ultrasound channel data.

18. The method of claim 17, further comprising:

providing second target beamformed data, wherein the second beamformed data is generated based on the first preset acquisition setting; and training the predictive network to produce the second target beamformed data from the test ultrasound channel data before training the predictive network to produce the first target beamformed data.

19. The method of claim 11, wherein the array of acoustic elements includes a one-dimensional array of acoustic elements.

20. The method of claim 11, wherein the array of acoustic elements includes a two-dimensional array of acoustic elements.

* * * * *